United States Patent
Tang et al.

(10) Patent No.: US 11,612,634 B2
(45) Date of Patent: Mar. 28, 2023

(54) PHARMACEUTICAL COMPOSITION AND METHOD FOR RELIEVING/ELIMINATING MORPHINE-INDUCED ANALGESIC TOLERANCE

(71) Applicant: XUZHOU MEDICAL UNIVERSITY, Xuzhou (CN)

(72) Inventors: Qiongyao Tang, Xuzhou (CN); Zhe Zhang, Xuzhou (CN); Chen Chen, Xuzhou (CN); Mingxi Tang, Xuzhou (CN); Yue Teng, Xuzhou (CN); Nan Zhou, Xuzhou (CN); Shaoxi Ke, Xuzhou (CN); Ping Dong, Xuzhou (CN); Jingjing Wang, Xuzhou (CN); Wanxin Su, Xuzhou (CN); Xiaohui Wang, Xuzhou (CN); Yanmei Xiao, Xuzhou (CN); Su Liu, Xuzhou (CN); Long Ma, Xuzhou (CN); Jun Gan, Xuzhou (CN); Xiaoxia Zhu, Xuzhou (CN); Sibei Ruan, Xuzhou (CN); Feng Ling, Xuzhou (CN)

(73) Assignee: XUZHOU MEDICAL UNIVERSITY, Xuzhou (CN)

( * ) Notice: Subject to any disclaimer, the term of this patent is extended or adjusted under 35 U.S.C. 154(b) by 0 days.

(21) Appl. No.: 17/548,717

(22) Filed: Dec. 13, 2021

(65) Prior Publication Data
US 2022/0168382 A1 Jun. 2, 2022

(30) Foreign Application Priority Data
Dec. 11, 2020 (CN) .......................... 202011458379.2
Mar. 26, 2021 (CN) .......................... 202110327612.1

(51) Int. Cl.
*A61K 38/10* (2006.01)
*A61K 31/485* (2006.01)
*A61P 25/04* (2006.01)

(52) U.S. Cl.
CPC ............ *A61K 38/10* (2013.01); *A61K 31/485* (2013.01); *A61P 25/04* (2018.01)

(58) Field of Classification Search
CPC .............................. A61K 38/10; A61K 31/485
See application file for complete search history.

(56) References Cited

U.S. PATENT DOCUMENTS

2006/0229434 A1   10/2006   Yokotagawa et al.

FOREIGN PATENT DOCUMENTS

| WO | 2018103761 A1 | 6/2018 | |
| WO | 2018108185 A1 | 6/2018 | |
| WO | WO-2018103761 A1 * | 6/2018 | ............... C07K 7/06 |

OTHER PUBLICATIONS

PubChem [Internet]. Bethesda (MD): National Library of Medicine (US), National Center for Biotechnology Information; 2004-. PubChem Compound Summary for CID 5288826, Morphine; [cited Jun. 1, 20226]. Available from: https://pubchem.ncbi.nlm.nih.gov/compound/Morphine (Year: 2022).*
Medhurst, S. J, et al.A rat model of bone cancer pain. Pain, 96(2002), 129-140.
Bennett, G. J, et al. A peripheral mononeuropathy in rat that produces disorders of pain sensation like those seen in man. Pain, 33(1988), 87-107.
Alessandri-Haber N, et al.TRPC1 and TRPC6 Channels Cooperate with TRPV4 to Mediate Mechanical Hyperalgesia and Nociceptor Sensitization. Journal of Neuroscience, 2009.29(19), 6217-6228.

* cited by examiner

*Primary Examiner* — Lianko G Garyu

(57) ABSTRACT

Disclosed are a pharmaceutical composition and method for relieving/eliminating morphine-induced analgesic tolerance. The pharmaceutical composition includes a therapeutically effective amount of a short peptide and morphine as active ingredients, and a pharmaceutically-acceptable carrier. The short peptide is a peptide consisting of an amino acid sequence shown in SEQ ID NO: 1 or a pharmaceutically-acceptable salt thereof. In the method, the short peptide and morphine are administered to a subject simultaneously; or the short peptide is injected to the subject followed by administration of the morphine; or a pharmaceutical composition including the short peptide and morphine is administered to the subject.

11 Claims, 16 Drawing Sheets

Specification includes a Sequence Listing.

SEQUENCE LISTING

<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Trp Lys Cys Asn Pro Asn Asp Asp Lys Cys Cys Arg Pro Lys Leu Lys
1               5                   10                  15

Cys

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Lys Cys Asn Pro Asn Asp Asp Lys Ala Ala Arg Pro Lys Leu Lys
1               5                   10                  15

Cys

```
<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Trp Lys Cys Asn Pro Asn Asp Asp Lys Ala Ala Arg Pro Lys Leu Lys
1               5                   10                  15

Ala

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Trp Lys Cys Asn Pro Asn Asp Asp Lys Cys Arg
1               5                   10
```

PHARMACEUTICAL COMPOSITION AND METHOD FOR RELIEVING/ELIMINATING MORPHINE-INDUCED ANALGESIC TOLERANCE

CROSS-REFERENCE TO RELATED APPLICATIONS

This application claims the benefit of priority from Chinese Patent Applications No. 202110327612.1, filed on Mar. 26, 2021; No. 202110341838.7, filed on Mar. 30, 2021; and No. 202011458379.2, filed on Dec. 11, 2020. The content of the aforementioned applications, including any intervening amendments thereto, is incorporated herein by reference in their entirety.

TECHNICAL FIELD

This application relates to biomedicine, and more particularity to a pharmaceutical composition and method for relieving/eliminating morphine-induced analgesic tolerance.

BACKGROUND

Opioids, as commonly-used analgesics in clinical, will induce a physiological tolerance and dependence after repeated administration, clinically manifested as analgesic tolerance. Specifically, the analgesic effect gradually weakens and even disappears after the long-term exposure to the opioids, and a higher dosage is required to reach the previous analgesic effect. Morphine is a representative prescribed opioid analgesic that can rapidly alleviate a wide variety of pain including refractory mechanical pain, neuropathic pain and cancer pain. Nevertheless, the long-term exposure will produce severe drug tolerance, and in this case, an increased dosage is required, which will further lead to the occurrence of drug addiction. An increased morphine administration may be accompanied by exacerbated pain instead, limiting the clinical application.

At present, the clinical measures to prevent and treat an opioid tolerance are mainly opioid reduction and opioid replacement. Several therapies, such as the combined use of low-dose opioid receptor antagonists or cholecystokinin (CCK) receptor antagonists and N-methyl-D-aspartic acid (MDMA) receptor antagonists, are still in preclinical or early clinical trial stage. It has been less reported about the mechanism of the morphine tolerance and its clinical therapies, and there is still a lack of effective clinical strategies to inhibit the development of morphine tolerance.

Therefore, it is urgently needed to develop an adjuvant for opioids (e.g., morphine), which is capable of relieving/eliminating the morphine analgesic tolerance while maintaining its analgesic activity.

SUMMARY

In order to overcome the deficiencies in the existing analgesic drugs, this application provides a pharmaceutical composition and method for relieving/eliminating morphine-induced analgesic tolerance to effectively and stably relieve/eliminate the morphine-induced analgesic tolerance while maintaining its analgesic activity.

The technical solutions of the present disclosure are described as follows.

In a first aspect, this application provides a pharmaceutical composition for relieving/eliminating morphine-induced analgesic tolerance, comprising:

a therapeutically effective amount of a short peptide and morphine as active ingredients; and a pharmaceutically-acceptable carrier;

wherein the short peptide is a peptide consisting of an amino acid sequence shown in SEQ ID NO: 1 or is a pharmaceutically-acceptable salt thereof.

In a second aspect, this application provides a method for relieving/eliminating morphine-induced analgesic tolerance in a subject in need thereof, comprising:

simultaneously administering a short peptide and morphine to the subject; or administering the short peptide to the subject followed by administration of the morphine; or administering a pharmaceutical composition to the subject;

wherein the pharmaceutical composition comprises:

a therapeutically effective amount of the short peptide and morphine as active ingredients; and a pharmaceutically-acceptable salt or carrier; and the short peptide is a peptide consisting of an amino acid sequence shown in SEQ ID NO: 1 or a pharmaceutically-acceptable salt thereof.

In some embodiments, the subject is human or animal.

In some embodiments, a type of pain for the morphine to relieve is inflammatory pain; and an administration dose of the short peptide for animal is not less than 0.05 µg/kg.

In some embodiments, the administration dose of the short peptide for animal is 0.05-0.10 µg/kg.

In some embodiments, an administration dose of the short peptide for human is 1/6.3-1/10 times an administration dose of the short peptide for animal.

In some embodiments, a type of pain for the morphine to relieve is neuropathic pain; and an administration dose of the short peptide is not less than 0.01 µg/kg.

In some embodiments, the administration dose of the short peptide is 0.01-0.40 µg/kg.

In some embodiments, an administration dose of the short peptide for human is 1/6.3-1/10 times an administration dose of the short peptide for animal.

In some embodiments, a type of pain for the morphine to relieve is bone cancer pain (BCP); and an administration dose of the short peptide is not less than 0.20 µg/kg.

In some embodiments, the administration dose of the short peptide is 0.20-0.40 µg/kg.

In some embodiments, an administration dose of the short peptide for human is 1/6.3-1/10 times an administration dose of the short peptide for animal.

Compared to the prior art, the present disclosure has the following beneficial effects.

In the method provided herein for relieving/eliminating morphine analgesic tolerance, the short peptide P10581 and morphine are administered simultaneously; or the short peptide P10581 is injected, and then the morphine is administered; or a pharmaceutical composition including the short peptide P10581 and morphine is administered to the subject in need, such that the morphine analgesic tolerance can be effectively and stably relieved/eliminated while maintaining the analgesic activity of the morphine. The pharmaceutical composition and method provided herein provide references for the clinical treatment of morphine tolerance and development of related drugs.

The summary is provided to enable those skilled in the art to understand the technical solutions of this disclosure and implement the invention according to the description. The disclosure will be described in detail below with reference to embodiments to render objects, features and advantages of the present disclosure clearer.

BRIEF DESCRIPTION OF THE DRAWINGS

The accompanying drawings are merely illustrative of the embodiments of the disclosure and related principles, applications, features, and effects, and should not be considered as limitations to this application.

DETAILED DESCRIPTION OF EMBODIMENTS

Figure 1A:
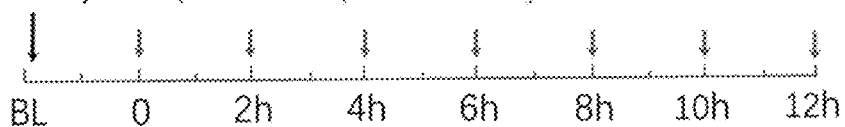
FIG. 1A schematically depicts injection time points of carrageenan (Carr, marked by long arrow), a short peptide P10581 (Peptide, marked by short arrow) and morphine (marked by short arrow)

This disclosure will be described in detail below with reference to embodiments and drawings to make technical solutions, features, objects and advantages of the disclosure clearer. The detailed implementation of the technical solutions of the disclosure is described below, but is not intended to limit the disclosure.

In this application, a short peptide provided herein is named P10581 and has the following amino acid sequence:

P10581: WKCNPNDDKCCRPKLKC (as shown in SEQ ID NO:1).

The short peptide P10581 is derived from two loops located in loop 2 and loop 3 of a spider venom GsMTx4. The short peptide P10581 can be prepared by chemical synthesis or recombination technology, and it can be fused with a protein, coupled with a polymer and also linked to a carrier.

The short peptide P10581 can be administered in a form of pharmaceutically-acceptable salt. In an embodiment, the pharmaceutically-acceptable salts are those formed with a pharmaceutically-acceptable organic acid, a polymeric acid, or an inorganic acid, where the organic acid includes acetic acid, 2-hydroxypropanoic acid, maleic acid, citric acid, malic acid, ascorbic acid, succinic acid, benzoic acid, salicylic acid, methanesulfonic acid, toluenesulfonic acid, trifluoroacetic acid and pamoic acid; the polymeric acid is tannic acid or carboxymethyl cellulose; and the inorganic acid is a halogen acid (such as hydrochloric acid), sulfuric acid or phosphoric acid. The pharmaceutically-acceptable salt can be obtained by any method well known to those of ordinary skill in the art.

The short peptide P10581 involved herein has an antinociceptive effect, and can quickly relieve multiple types of pain, and this analgesic effect can last for more than 12 h (acute) or 9 days (chronic). The short peptide P10581 also exhibits an excellent analgesic tolerance. Moreover, it has been surprisingly found that the low-dose short peptide P10581 can effectively relieve or even eliminate the morphine-induced analgesic tolerance.

In this application, the pain related to the analgesic tolerance that can be relieved or even eliminated by the short peptide P10581 includes headache, idiopathic pain, chronic pain (such as moderate to moderately sever chronic pain), inflammatory pain, neuropathic pain, fibromyalgia, regional pain (such as temporomandibular joint pain, toothache, backache and post-surgical pain) and allodynia caused by cancer (such as bone cancer, lung cancer, breast cancer, prostate cancer and ovarian cancer). As exemplarily described below, inflammatory pain, neuropathic pain and BCP models are built to merely describe the technical solutions of the disclosure in detail, but are not intended to limit the scope of the disclosure.

This application provides a pharmaceutical composition for relieving/eliminating morphine analgesic tolerance, including:

a therapeutically effective amount of a short peptide and morphine as active ingredients; and a pharmaceutically-acceptable carrier;

where the short peptide is a peptide consisting of an amino acid sequence shown in SEQ ID NO: 1 or a pharmaceutically-acceptable salt thereof.

In an embodiment, the pharmaceutically-acceptable carrier is selected from the group consisting of solvent, diluent, suspending agent, emulsifying agent, antioxidant, pharmacological preservative, coloring agent, flavor, medium, oily substrate, excipient and a combination thereof. The pharmaceutically-acceptable carrier can be used conventionally, and its composition and dosage can be experimentally determined as require, are not particularly limited herein.

In an embodiment, the pharmaceutical composition can be prepared in various pharmaceutically-acceptable forms, including liquid, semi-solid and solid dosage form, such as liquid solution (e.g., injection solution, infusion solution and oral solution), dispersion, suspension, powder, tablet, pill, pulvis, granule, liposome and suppository, and the dosage form can be determined according to the administration route and therapeutic application. The short peptide and morphine should be evenly distributed in the pharmaceutical composition. Preferably, the pharmaceutical composition is an injection solution, including but not limited to: subcutaneous injection solution, intraperitoneal injection solution and intrathecal injection solution.

In an embodiment, the pharmaceutical composition can be administered parenterally (such as intravenous injection, subcutaneous injection, intraperitoneal injection and intramuscular injection). The terms "parenteral administration" and "administered parenterally" refer to administration routes other than enteral administration and topical administration, which are usually performed by injection, including but not limited to: intravenous, intramuscular, intra-arterial, intrathecal, intracapsular injection and infusion, intravitreal, intranasal, intravertebral, intracardiac, intradermal, intraperitoneal, intra-abdominal, transtracheal, subcutaneous, subepidermal, intra-articular, subcapsular, subarachnoid, intraspinal, epidural and intrasternal injection and infusion.

In an embodiment, the pharmaceutical composition can be administered enterally, such as gastrointestinal administration and oral administration. For example, the pharmaceutical composition can be administered in a form of tablets, capsules, caplets, pills, powders, drops, suspensions, solutions, pastes, gels and so on. The enteral administration is performed by gastric tube feeding, duodenal tube feeding, gastrostomy and rectal administration in a form of suppositories or enemas.

In an embodiment, the pharmaceutical composition can be administered topically, such as at the site of pain. The topical administration includes epidermal administration, intranasal administration, inhaled administration and vaginal administration. The pharmaceutical composition can be administered to the skin (such as burns, blisters and wounds), lips, gums, teeth, oral cavity, eyes, ears, nail bed and throat. For the topical administration, the pharmaceutical composition can be prepared into cream, gel, lotion and ointment.

In an embodiment, the pharmaceutical composition includes a "therapeutically effective amount" of the short peptide provided herein. In this application, the effective amount (including dose and concentration) of the short peptide is not particularly limited. The effective amount can be determined according to the actual therapeutical effect. If more than one drug is used (e.g., short peptide+morphine, short peptide+other opioids, etc.), the effective amount is determined according to the combined effect. Moreover, the therapeutically effective amount is also related to the type of pain, disease condition, age, gender and body weight as well as an ability of the drug to induce a desired response (such as analgesic effect) in vivo. In addition, the therapeutically effective amount also refers to an amount in which the therapeutically beneficial effect of the pharmaceutical composition exceeds any toxic or harmful effects. In the following embodiments, the "therapeutically effective amount" is exemplarily illustrated with the short peptide P10581, and the optimal therapeutically effective amount ranges for inflammatory pain, neuropathic pain and BCP are provided, but are not intended to limit the scope of the disclosure.

This application further provides a method for relieving/eliminating the morphine-induced analgesic tolerance in a subject in need thereof, including:

simultaneously administering a short peptide and morphine to the subject; or administering the short peptide to the subject followed by administering the morphine; or administering a pharmaceutical composition to the subject;

where the pharmaceutical composition includes a therapeutically effective amount of the short peptide and morphine as active ingredients; and a pharmaceutically-acceptable carrier; and the short peptide is a peptide consisting of an amino acid sequence shown in SEQ ID NO: 1 or a pharmaceutically-acceptable salt.

As used herein, the terms "subject", "patient" or "individual" are interchangeable to refer to human or animal. For example, the animal subject can be mammals, primates (e.g., monkeys), domestic animals (e.g., horses, cattle, sheep, pigs and goats), companion animals (e.g., dogs and cats), laboratory test animals (e.g., mice, rats, guinea pigs and birds), animals of veterinary significance or animals of economic significance. In an embodiment, the "subject", "patient" or "individual" is human or animal treated with the opioids for acute or chronic pain. In the following embodiments, a rat pain model is established as a treatment object, but is not intended to limit the scope of the disclosure. The concentration/dose of the drug (short peptide) administered is the optimal therapeutically effective amount, and also is not intended to limit the scope of the disclosure.

In an embodiment, a type of pain for the morphine to relieve is inflammatory pain. An administration dose of the short peptide for animal is not less than 0.05 μg/kg, preferably 0.05-0.10 μg/kg.

In an embodiment, a type of pain for the morphine to relieve is neuropathic pain. An administration dose of the short peptide is not less than 0.01 μg/kg, preferably 0.01-0.40 μg/kg.

In an embodiment, a type of pain for the morphine to relieve is BCP. An administration dose of the short peptide is not less than 0.20 μg/kg, preferably 0.20-0.40 μg/kg.

In an embodiment, an administration dose of the short peptide for human is 1/6.3-1/10 times that of the short peptide for animal.

In the above-mentioned embodiments, the given dose for humans and animals is the optimal therapeutically effective amount for inflammatory pain, neuropathic pain and BCP, but is not intended to limit the scope of the disclosure. The therapeutically effective amount of the short peptide P10581 can be adjusted according to the following factors: a type of pain, disease condition, age, gender and body weight as well as an ability of the drug to induce a desired response (such as analgesic effect) in vivo.

The disclosure will be described in detail below with reference to the embodiments.

Unless otherwise specified, the materials and reagents in the following embodiments are available commercially, and the experiments are carried out using conventional methods. The first position of each peptide sequence in the sequence listing is the N-terminal amino acid residue, and the last position is the C-terminal amino acid residue unless otherwise specified. The following experiments are designed following the randomized and double-blind experimental principle.

1. Experimental Animals, Materials and Instruments

Healthy male adult Sprague-Dawley (SD) rats (at least 8 weeks old, purchased from the Experimental Animal Center of Xuzhou Medical University), weighing 180-220 g, were adopted to establish an inflammatory pain rat model and a neuropathic pain rat model.

0.1 g of Carrageenan (abbreviated as Carr, Sigma) was dissolved in 10 mL of 0.9 wt % normal saline to prepare 1% Carr solution, which was dispensed into 10 EP tubes and stored at −20° C. The Carr solution was placed on ice half an hour before use.

The mechanical hyperalgesia of rats was measured by 38500-pressure application measurement (PAM) system (Ugo Basile Biological Research Apparatus, Comerio-Varese, Italy), which consisted of a hand-held part and an integrated electronic part. The hand-held part was a force sensor which was designed according to a Randall-Selitto algesimeter. The integrated electronic part was configured to automatically record a maximum PWT applied to the left hind paw of the rats.

Healthy female young SD rats and healthy female adult SD rats (purchased from the Experimental Animal Center of Xuzhou Medical University), respectively weighing 90-100 g and 180-220 g, were adopted to establish a BCP rat model.

Walker 256 mammary gland carcinoma cells were purchased from Shanghai Institute of Biomedical Engineering.

2. Preparation of Experimental Animal Model

The inflammatory pain model, neuropathic pain model and BCP model adopted herein were well recognized as classical models for pain research.

(1) Preparation of Inflammatory Pain Rat Model

The Carr-induced inflammatory pain model was built according to a published method (Alessandri-Haber N, et al. Neurosci. Vol 29(19), pp. 6217-6288, 2009) for evaluating an analgesic effect of drugs administered by intraplantar injection. Specifically, 6 μL of 1 wt % Carr solution was injected into the rats between the $2^{nd}$ and $3^{rd}$ toes of a left hind paw to induce hyperalgesia, which was manifested as plantar swelling and a declined pain threshold of the rats within 1 hour after the injection. Those rats with a PWT lower than 100 gf were considered to be a desired Carr-induced inflammatory pain model, those rats with the PWT higher than 100 gf was removed.

(2) Preparation of Neuropathic Pain Rat Model

The chronic constriction nerve injury (CCI)-induced neuropathic pain rat model was built according to a published method (Bennett G J, et al. Pain, 1988). The experimental rats were anesthetized by intraperitoneal injection of 10 wt % chloral hydrate (300 mg/kg), and then placed on a super-clean bench, and the operation area was disinfected with iodophor. An oblique incision was made along a muscle texture in a dorsal limb of a left lower limb of the rat, and then a middle-superior segment of the sciatic nerve trunk was exposed through the blunt separation between biceps femoris muscles, and four ligations (with a spacing of 1 mm) were made at the bifurcation of the sciatic nerve with 4-0 silk sutures pre-soaked in sterile water for 15 min.

The ligation tightness should be adjusted to cause slight twitching of a leg on an operated side of the rat without affecting the blood circulation of the epineurium. The wound was sutured layeredly and wiped with iodophor according to the postoperative situation. The rats were transferred back into a cage for rest upon fully recovering. The PWT was measured 5 days after modeling, where those with a significant lower PWT were considered as successful neuropathic pain rat models, and the undesirable rats were excluded.

(3) Preparation of Bone Cancer Pain (BCP) Rat Model

The tumor cell implantation (TCI) surgery was performed according to the method proposed by Medhurst S J, et al (Medhurst S. J., Walker K., Bowes M., Kidd B. L., Glatt M., Muller M., et al. (2002). A rat model of bone cancer pain. *Pain* 96 129-140). Walker 256 mammary gland carcinoma cells were transferred from a liquid nitrogen tank, thawed quickly in a 37° C. water bath and loaded into a centrifugal tube. Then the cells were added with an appropriate amount of normal saline and centrifuged at 1200 r/min for 6 min. The supernatant was discarded, and the cells were washed again, and suspended with phosphate buffered saline (PBS) to $1 \times 10^7$/mL. Young female SD rats, weighing 90-100 g, were intraperitoneally injected with 0.5 mL of mammary gland carcinoma cells, and a large amount of ascites occurred after 6-7 days of the injection. 10 mL of ascites was extracted and centrifuged for 5 min. The precipitate was washed with normal saline and then diluted with PBS to $1 \times 10^5$/mL. The rats were anesthetized with 10% chloral hydrate and shaved, and a 1-cm incision was made in the upper half skin of the right tibia to expose the bone surface with a minimal damage to the surrounding muscle or blood vessels. The bone was pierced with a 4 # needle at 5 mm below a knee joint distal to an epiphysial growth plate, and the needle was inserted to a depth so that it can be pushed into the medullary cavity. The needle was then removed, and a 10 mL microsyringe needle containing cells to be injected was inserted into the medullary cavity, determining whether the needle was located in the medullary cavity by withdrawal. 5 mL ($1 \times 10^5$/mL) of cancer cells were injected into the medullary cavity, and whether there are cells or blood leaking out from the injection site was observer.

The needle was kept in the medullary cavity for 1 min and then was withdrawn to enable the full cell spreading, and the injection site was pressed by a cotton swab for 1 min and closed with bone cement. The wound was sutured and treated with penicillin powder. The PWT was measured 3 days after modeling, where those rat models with a significant lower PWT were considered as successful BCP rat models, and the undesirable models were removed. The PWT test results of the BCP rat model were illustrated in FIG. 13, from which it can be observed that the PWT of the BCP model reached the peak (i.e., the minimal PWT) from the $18^{th}$ day to the $35^{th}$ day.

In the case of unsuccessful modeling, additional experiments were performed to ensure that there were at least 5-8 rats per group for statistical analysis.

3. Statistical Analysis

The graphs were plotted using Grapher 5 software, and the statistical analysis was completed using the SPSS16.0 software with data expressed as mean±standard error (Mean±SE) ($\alpha=0.05$, $P<0.05$). The means of two independent samples was compared by t-test, and the t' test was adopted in the case of unequal variances. The PWT test results of multiple samples at the same time point were compared by Least-Significant Difference (LSD) of one-way analysis of variance or Tamhane T2 test in the case of unequal variances. The PWT test results of multiple samples at different time points were compared by two-way analysis of variance.

The experiments involved herein all followed the randomized double-blind design principle.

Experimental Example 1 Analgesic Effect of Short Peptide P10581 and Morphine on Mechanical Hyperalgesia in Inflammatory Pain Rat Model and Analgesic Tolerance The analgesic effect of the short peptide P10581 and morphine on mechanical hyperalgesia in an inflammatory pain rat model and the analgesic tolerance were investigated herein, respectively, through the following steps.

(S1) A total of 18 healthy adult SD rats, weighing 180-220 g, were selected, numbered on tails and placed in the same cage.

(S2) The rats were maintained in a measuring room for 2 h for adaptation. After the rats became quiet, the tapered tip of the 38500-PAM system was aimed at the plantar center of the left hind paw of the rats to measure PWT at a constant force rate (30 gf/s), with a maximum measurement time of 15 s (a measured value greater than 450 gf will cause damage to rats).

(S3) The PWT was recorded when a left hind paw of the rats showed withdrawal reflex, and if the rat did not generate the withdrawal response after 15 s, the measurement was stopped. The measurement was repeated 3-5 times for each rat with an interval of 5-10 min. The results of multiple PWT measurements were averaged as the Baseline (BL) (unit: g).

After that, 6 μL of 1 wt % Carr was intradermally injected into the plantar surface of the hind paw to build an inflammatory pain rat model.

(S4) The PWT of the left hind paw of each rat was measured 1 h after the Carr injection. Rats with a higher inflammatory threshold and rats with a lower inflammatory threshold were mixed and equally divided into three groups (group A, group B and group C), each for six rats, such that any two groups of rats had similar distribution of inflammatory threshold. The groups A, B and C were intradermally injected with normal saline, 5 mg/kg of morphine and 2 μg/kg of the short peptide P10581, respectively, at the plantar surface of the left hind paw. 1 h later, the PWT of the left hind paw of the rats in each group was measured 3-5 times at an interval of 5-10 min. The multiple PWT measurement results were averaged as the practical PWT (unit: g). Then the drug was injected every 2 h according to the above-mentioned administration dose and time, and the corresponding PWT was recorded (six injections in total).

Figure 1B:
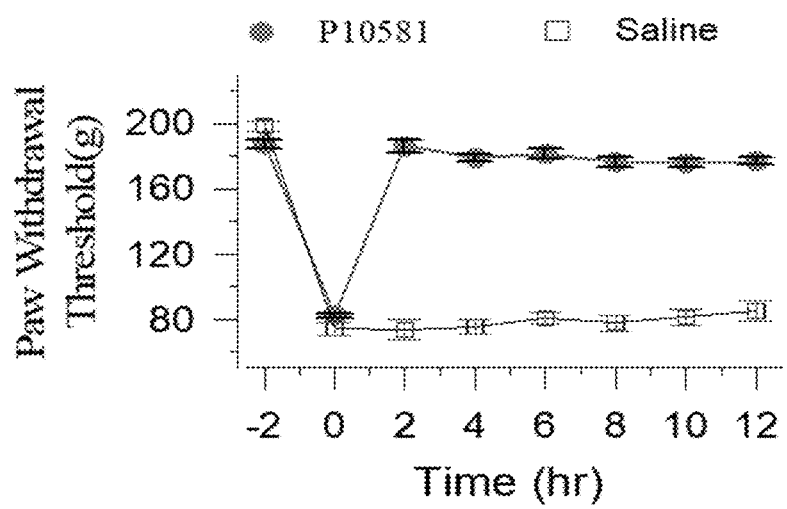
FIG. 1B illustrates test results of inhibitory effect of the short peptide P10581 on inflammatory pain in rats and its analgesic tolerance.
Figure 1C:
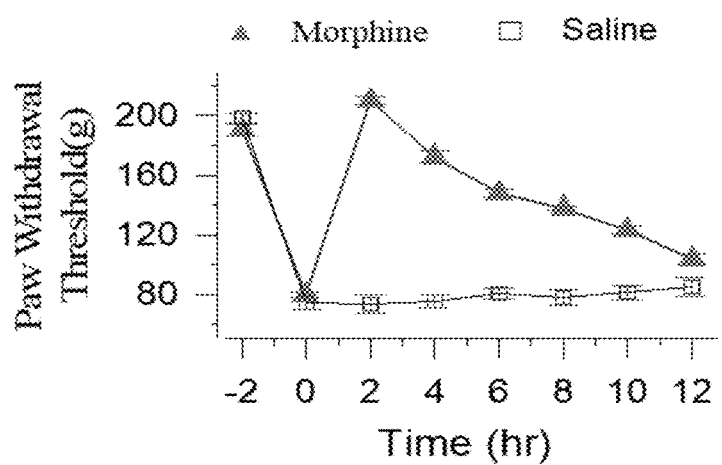
FIG. 1C illustrates test results of inhibitory effect of the morphine on inflammatory pain in rats and its analgesic tolerance.
Figure 2:
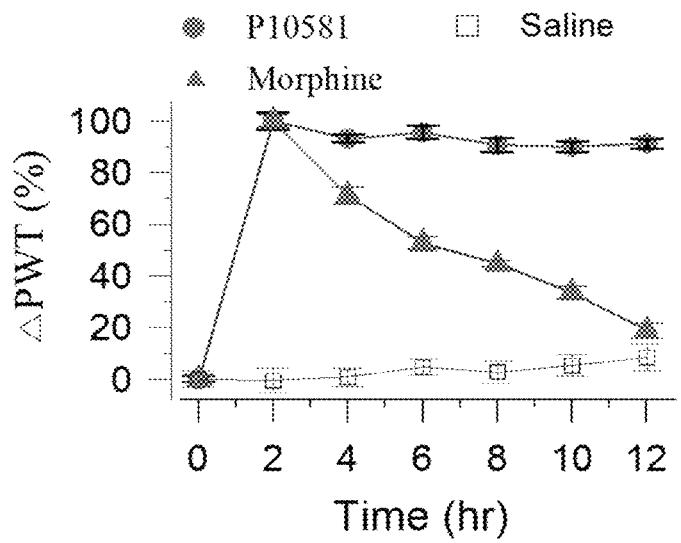
FIG. 2 illustrates comparison of the analgesic tolerance of the short peptide P10581 and the morphine for inflammatory pain in rats after normalization.

FIG. 1A schematically depicted injection time points of the Carr, the short peptide P10581 (Peptide) and morphine, where a long arrow indicated the injection time point of the Carr, and short arrows indicated the injection time points of the short peptide P10581 (Peptide) and morphine. As shown in FIG. 1A, in this embodiment, the short peptide P10581 and morphine were intradermally (i.d.) injected into the plantar surface every 2 h, respectively. FIG. 1B illustrated an analgesic effect of the short peptide P10581 on inflammatory pain in rats and its analgesic tolerance. FIG. 1C illustrated an analgesic effect of the morphine on inflammatory pain in rats and its analgesic tolerance. As illustrated in FIG. 2, the short peptide P10581 was compared with the morphine in terms of the analgesic tolerance for inflammatory pain in rats after normalization.

As shown in FIGS. 1A-C and 2, the short peptide P10581 of the disclosure can completely reverse the Carr-induced inflammatory pain threshold and the analgesic effect can last for more than 12 h, which indicated that the short peptide P10581 (2 μg/kg) exhibited an excellent relieving effect on the mechanical pain in rats without developing the analgesic tolerance. By contrast, the morphine (5 mg/kg) showed a gradually declined analgesic effect with the increase in the number of injections, which demonstrated the occurrence of the morphine-induced analgesic tolerance.

Experimental Example 2 Analgesic Effect of Low-Dose Short Peptide P10581 with on Mechanical Hyperalgesia in Inflammatory Pain Rat Model and Effect of Low-Dose Short Peptide P10581 on Morphine Analgesic Tolerance The analgesic effect of the short peptide P10581 in a dose of 0.05 μg/kg-0.10 μg/kg on mechanical hyperalgesia in the inflammatory pain rat model and an effect of the short peptide P10581 on the morphine analgesic tolerance were investigated herein.

The inhibitory effect of the short peptide P10581 on the mechanical hyperalgesia in rats was evaluated basically according to the steps in Experimental Example 1.

(1) 24 healthy adult SD rats, weighing 180-220 g, were selected, reinjected with 6 μL of a 1 wt % Carr solution and divided into 4 groups randomly and averagely (i.e., groups A-D). The group A was injected with normal saline; the group B was intradermally injected with 0.1 μg/kg of the short peptide P10581 through the plantar surface of the left hind paw; the group C was intradermally injected with 0.1 μg/kg of the short peptide P10581 and then with 5 mg/kg of morphine 30 min later through the plantar surface of the left hind paw; and the group D was intradermally injected with 0.05 μg/kg of the short peptide P10581, and then with 5 mg/kg of morphine 30 min later through the plantar surface of the left hind paw. 1 h later, the PWT of each group was recorded when the mechanical withdrawal of the left hind paw occurred, and each rat was measured 3-5 times at an interval of 5-10 min.

(2) The drug was injected every 2 h according to the above-mentioned administration dose and time (seven times in total), and the PWT was recorded.

Figure 3:
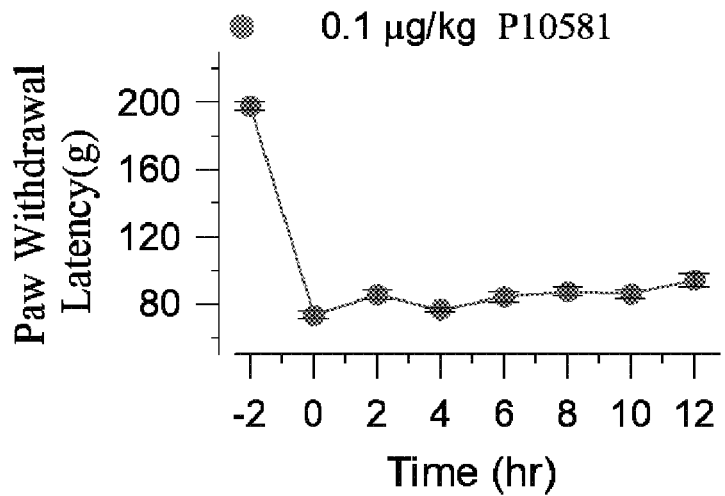
FIG. 3 illustrates test results of the analgesic effect of the short peptide P10581 in a low dose on inflammatory pain in rats.

The analgesic effect of the low-dose short peptide P10581 on inflammatory pain in rats was illustrated in FIG. 3. It can be observed that the short peptide P10581 (0.1 μg/kg) had no relieving effect on the hyperalgesia in rats, even after increased injections.

Figure 4A:
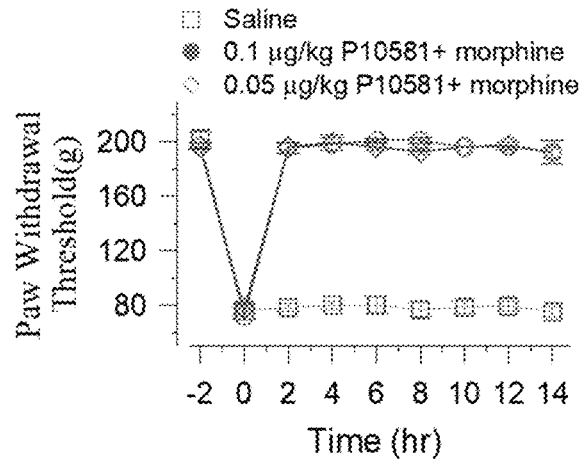
FIG. 4A illustrates actual test results of a relieving/eliminating effect of low-dose short peptide P10581 on the morphine analgesic tolerance for inflammatory pain in rats.

The relieving/eliminating effect of the low-dose short peptide P10581 (0.1 μg/kg and 0.05 μg/kg) on the morphine analgesic tolerance for mechanical hyperalgesia in rats was shown in FIG. 4A. It can be demonstrated that the morphine analgesic tolerance can be eliminated by the low-dose short peptide P10581 (0.1 μg/kg and 0.05 μg/kg); moreover, the eliminating effect was maintained over 14 h.

Figure 4B:
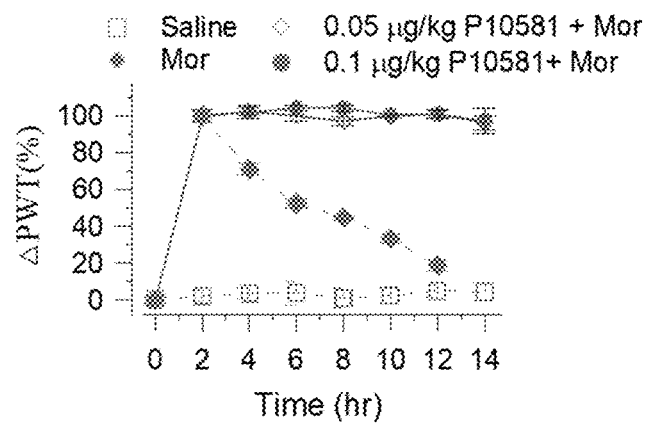
FIG. 4B illustrates normalized results of the relieving/eliminating effect of low-dose short peptide P10581 on the morphine analgesic tolerance for inflammatory pain in rats.

FIG. 4B illustrated normalized results of the relieving effect of the low-dose short peptide P10581 (0.1 μg/kg and 0.05 μg/kg) on the morphine analgesic tolerance for mechanical hyperalgesia in rats. As shown in FIG. 4B, the analgesic effect of the morphine continuously decreased in the absence of the short peptide P10581, which suggested the development of the morphine analgesic tolerance. Conversely, the analgesic effect of the morphine was maintained in the presence of the low-dose short peptide P10581 (0.1 μg/kg or 0.05 μg/kg), demonstrating that the short peptide P10581 can eliminate the morphine analgesic tolerance and this effect can be maintained over 14 h.

According to Experimental Examples 1-2, it can be concluded that in the presence of 0.05 μg/kg or more of the short peptide P10581, the morphine analgesic tolerance can be effectively alleviated, and when the administration dose reached 0.05-0.10 μg/kg, the morphine analgesic tolerance can be completely eliminated, and the analgesic effect of the morphine can be maintained. Surprisingly, the single administration of 2 μg/kg of the short peptide P10581 can produce excellent analgesic effect on inflammatory pain in rats without tolerance.

Thus, at a relatively low dose (0.05-0.10 μg/kg), the short peptide P10581 can completely eliminate the morphine analgesic tolerance for inflammatory pain, and the analgesic effect of the morphine can be maintained; and when the dose reached 2 μg/kg, the short peptide P10581 can exhibit an analgesic effect comparable to that of the morphine, and will not produce tolerance after repeated administrations.

Experimental Example 3 Effect of Cysteine in Short Peptide P10581 on Morphine Analgesic Tolerance The effect of cysteine in the short peptide P10581 on the morphine analgesic tolerance was evaluated using an inflammatory pain rat model.

(S1) By means of molecular biological techniques, two cysteine residues (Cys10 and Cys11) in the short peptide P10581 were replaced with alanine (Ala), and the resulting peptide was named P10581-1 (SEQ ID NO: 2).

(S2) Three cysteine residues (Cys10, Cys11 and Cys17) in the short peptide P10581 were replaced with alanine (Ala), and the resulting peptide was named P10581-2 (SEQ ID NO: 3).

```
P10581:
                    (as shown in SEQ ID NO: 1)
WKCNPNDDKCCRPKLKC;

P10581-1:
                    (as shown in SEQ ID NO: 2)
WKCNPNDDKAARPKLKC;

P10581-2:
                    (as shown in SEQ ID NO: 3)
WKCNPNDDKAARPKLKA.
```

The rat was injected with 6 μL of 1 wt % Carr to establish a Carr-induced inflammatory pain model, and the effect of the short peptides P10581, P10581-1 and P10581-2 on the morphine analgesic tolerance was analyzed according to Experimental Example 1.

Figure 5A:
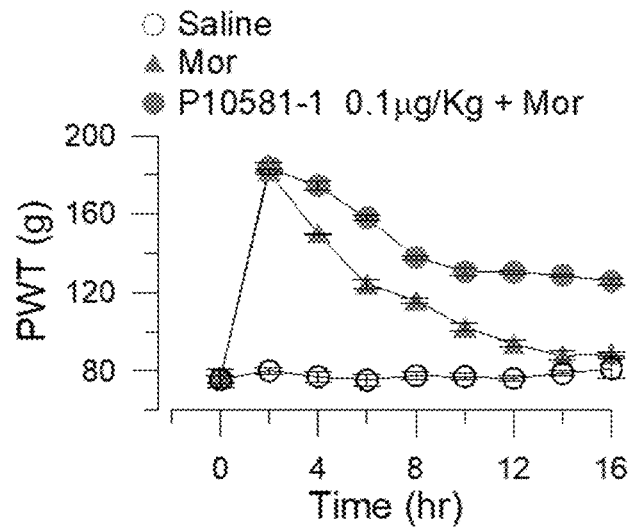
FIG. 5A illustrates test results of an effect of a short peptide P10581-1 on the morphine analgesic tolerance.
Figure 5B:
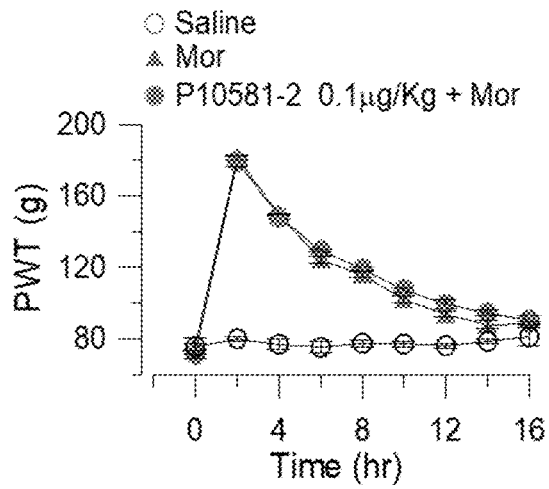
FIG. 5B illustrates test results of an effect of a short peptide P10581-2 on the morphine analgesic tolerance.
Figure 5C:
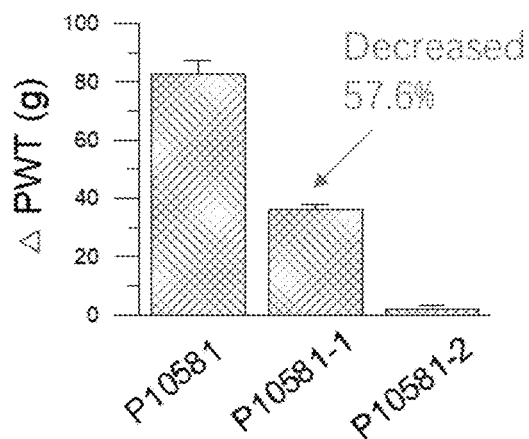
FIG. 5C illustrates comparison of effects of the short peptide P10581, the short peptide P10581-1 and the short peptide P10581-2 on the morphine analgesic tolerance after 8 injections.

FIGS. 5A-5C illustrated the effect of the short peptides P10581-1 and P10581-2 on the morphine analgesic tolerance. As shown in FIG. 5A, the short peptide P10581-1 obtained by replacing the two cysteine residues (Cys10 and Cys11) in the short peptide P10581 with alanine (Ala) can merely partially relieve the morphine analgesic tolerance. FIG. 5C showed comparison of effects of the short peptides P10581, P10581-1 and P10581-2 on the morphine analgesic tolerance after 8 injections. Compared to the short peptide P10581, the short peptide P10581-1 experienced a 57.6% decrease in the analgesic effect (FIG. 5C). Interestingly, the short peptide P10581-3 obtained by mutating the three cysteine residues (Cys10, Cys11 and Cys17) in the short peptide P10581 into alanine (Ala) had no relieving effect on the morphine analgesic tolerance (FIG. 5B).

As demonstrated above, the cysteine residues (Cys10, Cys11 and Cys17) in the short peptide P10581 played a crucial role in relieving/eliminating the morphine analgesic tolerance.

Experimental Example 4 Analgesic Effect of Short Peptide P10581 and Morphine on Mechanical Hyperalgesia in Neuropathic Pain Rat Model and their Analgesic Tolerances The analgesic effects of the short peptide P10581 and morphine on mechanical hyperalgesia in a neuropathic pain rat model and their analgesic tolerances were explored herein.

(S1) A total of 15 healthy adult SD rats, weighing 180-220 g, were selected, numbered on tails and placed in the same cage.

(S2) The rats were raised in a measuring room for 2 h for adaptation. After the rats became quiet, a tapered tip of the 38500-PAM system was aimed at the plantar center of the left hind paw of the rats to measure PWT at a constant force rate (30 gf/s), with a maximum measurement time of 15 s (a measured value greater than 450 gf will cause damage to rats).

(S3) The PWT was recorded when the left hind paw showed withdrawal reflex, and if the rat did not generate the withdrawal reflex after 15 s, the measurement was stopped. The measurement was repeated 3-5 times for each rat at an interval of 5-10 min, and the results were averaged. Then the rats were allowed to rest for several hours and then adopted to build a CCI-induced neuropathic pain model.

(S4) The PWT was measured on the morning of the $3^{rd}$ day and the $6^{th}$ day after the modeling, and those unsuccessful models were removed. And on the $6^{th}$ after the modeling, the successful rat models were randomly divided into 3 groups, where the group A was injected with normal saline; the group B was injected with 5 mg/kg of morphine; and the group C was intradermally injected with 8 μg/kg of the short peptide P10581 into the left hind paw. 1 h later, the PWT of each group was recorded when the left hind paw generated mechanical withdrawal. Each of the rats was measured 3-5 times at an interval of 5-10 min, and the PWTs were averaged as the actual PWT (unit: g). The drug injection was fixedly performed at 9:00 a.m. and 5:30 p.m. from the $6^{th}$ day to the $14^{th}$ day after modeling, and the PWT of each group was measured before and after administration every other day. On the $15^{th}$ day after modeling, the group B was injected with 8 μg/kg of the short peptide P10581 and the group C was injected with 5 mg/kg of the morphine, and the PWT of the group B and group C was recorded when the mechanical withdrawal occurred to the left hind paw.

Figure 6A:
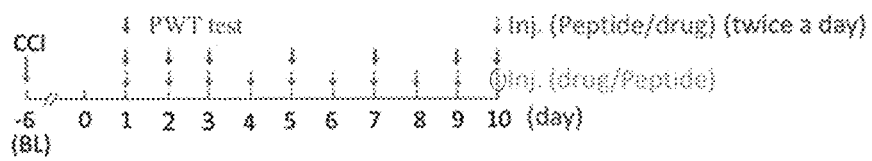
FIG. 6A schematically depicts a testing time point of a paw withdrawal threshold (PWT, marked by solid arrow), an injection time point of the short peptide P10581 (Peptide, marked by dashed arrow or arrow in a circle) and an injection time point of the morphine (drug, marked by dashed arrow or arrow in a circle), where an arrow with CCI (chronic constriction nerve injury) indicates a time point when a CCI neuropathic pain model rat is established.

FIG. 6A schematically depicted a testing time point of the PWT, and injection time points of the short peptide P10581 (Peptide) and morphine (drug), where an arrow with CCI indicated a modeling time point; a solid arrow indicated a testing time point of the PWT; dotted arrows indicated the injection time point of the short peptide P10581 (Peptide) or morphine (drug); and an arrow in circle indicated the injection time point of the morphine (drug) or the short peptide P10581 (Peptide).

Figure 6B:
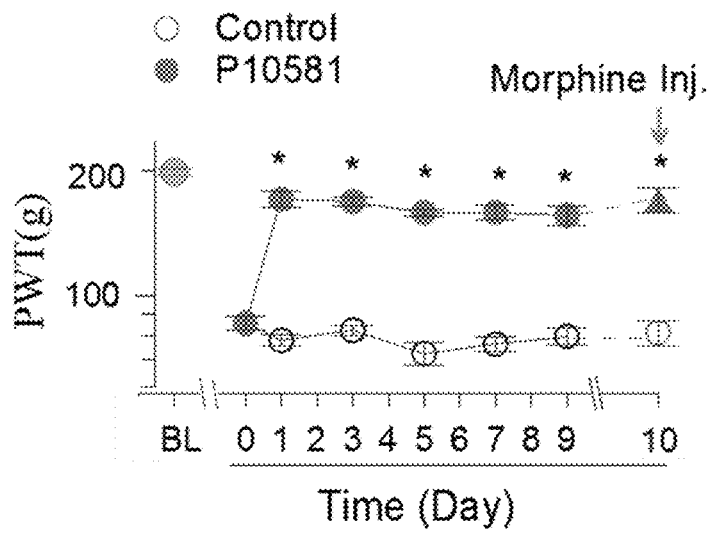
FIG. 6B illustrates test results of an effect of repeated injection of the short peptide P10581 followed by morphine injection on the neuropathic pain in rats.

The alleviation effect of repeated injection of the short peptide P10581 followed by morphine injection on neuropathic pain in rats was illustrated in FIG. 6B. The neuropathic pain was alleviated after repeated intradermal injections of the short peptide P10581 (8 μg/kg, and twice a day), and no analgesic tolerance occurred. In addition, after the intradermal morphine injection (5 mg/kg) on the $10^{th}$ day, the same analgesic effect was still kept.

Figure 6C:
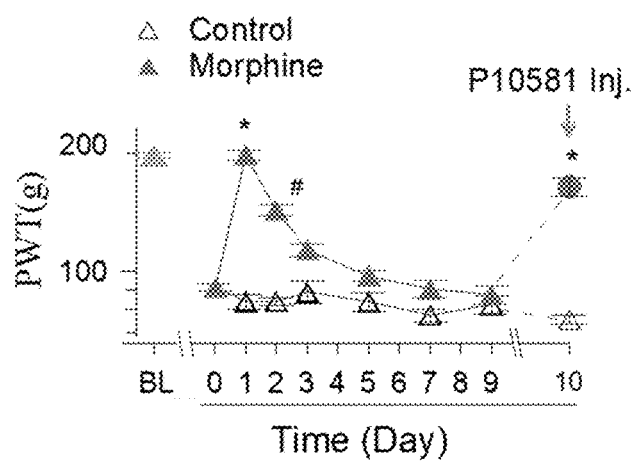
FIG. 6C illustrates test results of an effect of repeated injection of the morphine followed by injection of the short peptide P10581 on the neuropathic pain in rats.

The alleviation effect of repeated injection of morphine followed by injection of the short peptide P10581 on neuropathic pain in rats was illustrated in FIG. 6C, from which it can be found that the morphine exhibited a gradually-declined analgesic effect after repeated rejection (5 mg/kg, twice a day), and eventually lost the analgesic effect (analgesic tolerance). Surprisingly, after the intradermal injection of the short peptide P10581 (8 μg/kg) on day 10, the neuropathic pain threshold of rats can be reversed, and the analgesic effect of the short peptide P10581 was not affected by the morphine tolerance.

Figure 7:
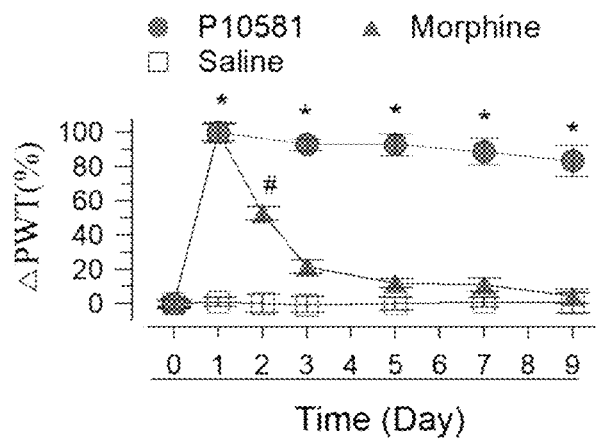
FIG. 7 illustrates a comparison of analgesic tolerances of the morphine and the short peptide P10581 for neuropathic pain in rats after normalization.

FIG. 7 illustrated the comparison of the analgesic tolerance of the morphine and the short peptide P10581 for neuropathic pain in rats after normalization. As shown in FIG. 7, with regard to the neuropathic pain in rats, the repeated injection of morphine induced the analgesic tolerance, while no analgesic tolerance was produced after the injection of the short peptide P10581.

Experimental Example 5 Difference in Dose Dependence of Neuropathic Pain in Rats Before and After Repeated Administration of High-Dose Short Peptide P10581

The difference in the dose dependence of neuropathic pain in rats before and after repeated administration of high-dose short peptide P10581 for 9 days (twice a day) was evaluated herein.

The experiment in this example was performed basically according to the steps of Experimental Example 4.

(1) 30 healthy adult SD rats, weighing 180-220 g, were selected to build a CCI-induced neuropathic pain model. On the $8^{th}$ day after the modeling, successfully-established models were randomly divided into 6 groups, where the group A was injected with 0.45 μg/kg of the short peptide P10581; the group B was injected with 0.9 μg/kg of the short peptide P10581; the group C was injected with 1.8 μg/kg of the short peptide P10581; the group D was injected with 3.6 μg/kg of the short peptide P10581; the group E was injected with 7.2 μg/kg of the short peptide P10581; and the group F was injected with 8.5 μg/kg of the short peptide P10581. The PWT of each group was measured 1.5 h later.

(2) Each group was injected with 7.2 μg/kg of the short peptide P10581 at 5:30 p.m. on the $8^{th}$ day after modeling, and then continuously injected from the $9^{th}$ day to the $16^{th}$ day 16 (injected with 7.2 μg/kg of the short peptide P10581 at 9:00 a.m. and 5:30 p.m. a day). The PWT of rats before and after administration in the morning was measured every other day.

(3) On the $17^{th}$ day after modeling, the six groups were injected with different doses of the short peptide P10581, respectively, according to step (1). 1.5 h later, the PWT of each group was measured to evaluate the effect of dose.

Figure 8A:
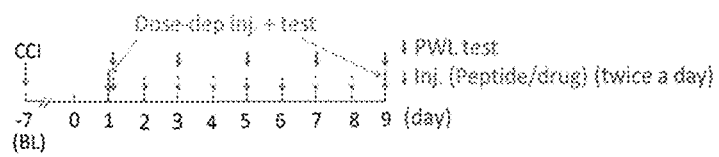
FIG. 8A schematically depicts a testing time point of PWT (marked by short solid arrow), injection time points of a series of doses of the short peptide P10581 (Peptide, marked by short dashed arrow) and an injection time point of the morphine (drug), where an arrow with CCI indicates a modeling time point; and a long arrow indicates a time period during which a high dose (7.2 µg/kg through intradermal injection (i.d.)) of the short peptide P10581 is injected.

FIG. 8A schematically depicted a testing time point of the PWT, and the injection time points of the short peptide P10581 (Peptide) and morphine, where an arrow with CCI indicated a modeling time point; a short solid arrow indicated a testing time point the PWT; a short-dotted arrow indicated the injection time point of the short peptide P10581 (Peptide) with different doses; and a long arrow indicated an injection time period of the high-dose short peptide P10581 (i.d. 7.2 μg/kg).

Figure 8B:
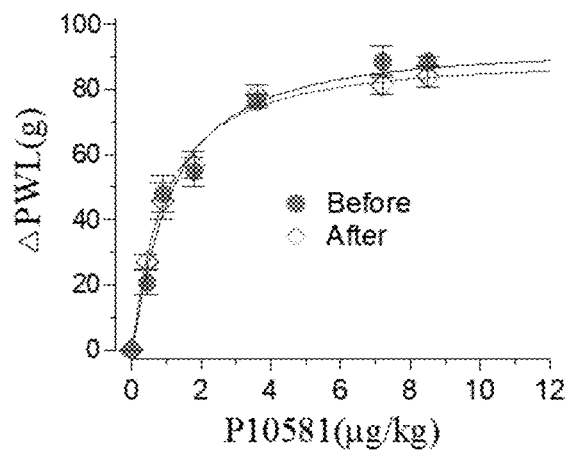
FIG. 8B illustrates test results of PWT of rats in groups A-F before and 9 days after repeated administration (twice a day) at an increased dose.

FIG. 8B illustrated test results of the PWT of groups A-F before and after 9-day repeated administration (twice a day) of the short peptide P10581 with an increased dose. The group E was taken as an example to illustrate the injection time point of the high-dose short peptide P10581 (7.2 μg/kg). It should be noted that the group E was injected with 7.2 μg/kg of the short peptide P10581 all the time. The test results of PWT of the group E before and after 9-day repeated administration with 7.2 μg/kg of the short peptide P10581 (twice a day) were shown in FIG. 8C, where an arrow (1) indicated a time point before the repeated intradermal administration of the high-dose short peptide P10581 (7.2 μg/kg); and an arrow (2) indicated a time point after the repeated intradermal administration of the high-dose short peptide P10581 (7.2 μg/kg).

Figure 8C:
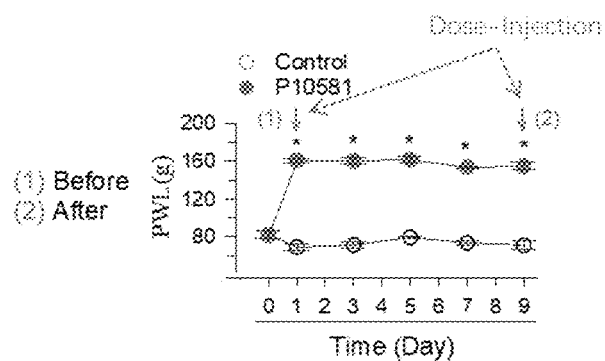
FIG. 8C illustrates test results of PWT of rats in group E before and 9 days after repeated administration (intradermally injected with 7.2 µg/kg of the short peptide P10581, twice a day), where an arrow (1) indicates a time point before the repeated administration; and an arrow (2) indicates a time point after the repeated administration.

It can be seen from FIGS. 8B-8C that no obvious change occurred to the PWT of each group after the repeated administration of the high-dose short peptide P10581, confirming that the analgesic effect of the short peptide P10581 on neuropathic pain in rats was not affected by the repeated administration (7.2 μg/kg and twice a day). As a consequence, it can be concluded that the short peptide P10581 will not induce the analgesic tolerance for neuropathic pain (without dose-dependence). This experiment further demonstrated that the analgesic effect of the short peptide P10581 on neuropathic pain will not be weakened by repeated administration. It should be noted that the analgesic effect of the short peptide P10581 on neuropathic pain in rats reached the peak under an administration dose of 7.2 μg/kg.

Figure 8D:
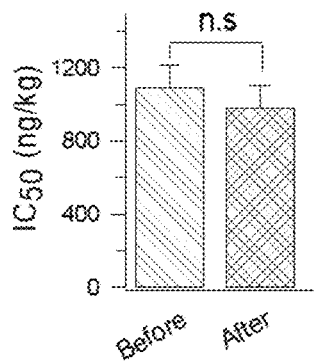
FIG. 8D illustrates a comparison of a half maximal inhibitory concentration ($IC_{50}$) before and after repeated administration of the high-dose short peptide P10581 (7.2 µg/kg through i.d.)

The comparison of a half maximal inhibitory concentration ($IC_{50}$) before and after repeated intradermal administration of the high-dose short peptide P10581 (7.2 μg/kg) was illustrated in FIG. 8D, from which it can be found that the repeated administration did not bring significant difference to the $IC_{50}$, further demonstrating that the repeated administration of the high-dose short peptide P10581 will not induce analgesic tolerance for the neuropathic pain in rats.

Experimental Example 6 Analgesic Effect of Low-Dose Short Peptide P10581 on Mechanical Hyperalgesia in Neuropathic Pain Rat Model and Effect of Low-Dose Short Peptide P10581 on Morphine Analgesic Tolerance An analgesic effect of the low-dose short peptide P10581 (0.1 μg/kg) on mechanical hyperalgesia in a neuropathic pain rat model and an effect of the low-dose short peptide P10581 on the morphine analgesic tolerance were evaluated herein.

This experiment 6 was performed basically according to the steps in Experimental Example 4.

(1) 15 healthy adult SD rats, weighing 180-220 g, were selected to build a CCI-induced neuropathic pain model. 6 days after the modeling, successful models were randomly divided into 3 groups, where the group A was injected with 0.1 μg/kg of the short peptide P10581; the group B was injected with 5 mg/kg of the morphine; and the group C was injected with 0.1 μg/kg of the short peptide P10581, and then with 5 mg/kg of the morphine 30 min later. 1 h later, the PWT of each group was recorded.

(2) Each group was injected with the drug in the afternoon on the $6^{th}$ day after the modeling, and from the $7^{th}$ day to the $12^{th}$ day, the drug administration was performed at 9:00 a.m. and 5:30 p.m. (5 mg/kg of morphine twice a day; and 0.1 μg/kg of the short peptide P10581 was administered 30 min before the morphine injection). The PWT of rats in each group before and after administration in the morning was measured every other day.

Figure 9A:
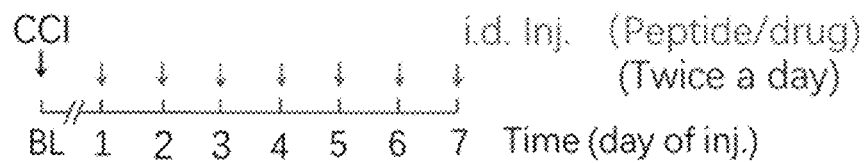
FIG. 9A schematically depicts injection time points of the low-dose short peptide P10581 (0.1 µg/kg) and morphine, where an arrow with CCI indicates a modeling time point; and other arrows indicate the injection time point of the short peptide P10581 (Peptide) or the injection time point of morphine (drug)

FIG. 9A schematically depicted injection time points of the low-dose short peptide P10581 (0.1 μg/kg) and morphine, where an arrow with CCI indicated a modeling time point, and other arrows indicated the injection time point of the short peptide P10581 (Peptide) or morphine (drug).

Figure 9B:
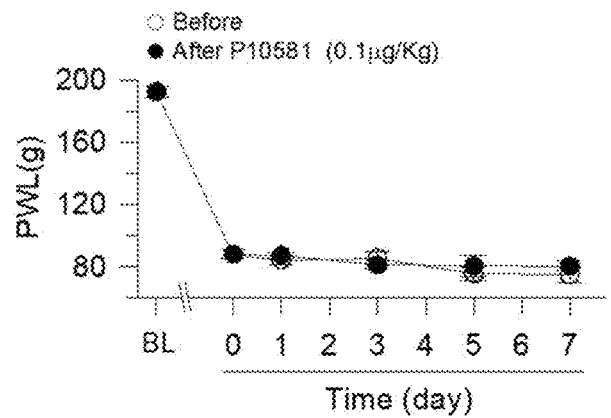
FIG. 9B illustrates the analgesic effect of the low-dose short peptide P10581 (0.1 µg/kg) on the neuropathic pain in rats.

The analgesic effect of the low-dose short peptide P10581 (0.1 μg/kg) on neuropathic pain in rats was shown in FIG. 9B, from which it can be observed that the intradermal administration of 0.1 μg/kg of the short peptide P10581 had no effect on the threshold of neuropathic pain in rats, and no significant analgesic effect was observed with the increase of the number of administrations, demonstrating that 0.1 μg/kg of the short peptide P10581 failed to generate an effective analgesic effect on the neuropathic pain in rats.

Figure 9C:
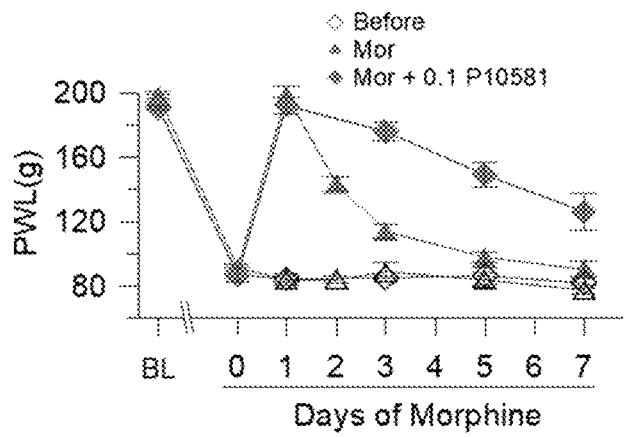
FIG. 9C schematically depicts an effect of the low-dose short peptide P10581 (0.1 µg/kg) on the morphine analgesic tolerance.

FIG. 9C schematically depicted an effect of the low-dose short peptide P10581 (0.1 μg/kg) on the morphine analgesic tolerance, where the group injected with morphine (Mor) was a positive control group. As shown in FIG. 9C, 0.1 μg/kg of the short peptide P10581 partially relieved the morphine analgesic tolerance for neuropathic pain in rats (group Mor+0.1 P10581). For example, on the $5^{th}$ day, the analgesic effect of the morphine on the neuropathic pain was restored by half.

Experimental Example 7 Analgesic Effect of Short Peptide P10581 (Low-Dose) in Different Doses on Mechanical Hyperalgesia in Neuropathic Pain Rat Model and Effect of Short Peptide P10581 in Different Doses on Morphine Analgesic Tolerance An analgesic effect of the low-dose short peptide P10581 (0.01 μg/kg-0.40 μg/kg) on mechanical hyperalgesia in a neuropathic pain rat model and its effect on the morphine analgesic tolerance were investigated herein.

This experiment was performed basically according to the steps of Experimental Example 4.

(1) 30 healthy adult SD rats, weighing 180-220 g, were selected to build a CCI-induced neuropathic pain model. Those successfully-established models were randomly divided into 6 groups on the $6^{th}$ day, where the groups A was injected with normal saline; and the groups B-F were injected with 0.01 µg/kg, 0.025 µg/kg, 0.1 µg/kg, 0.2 µg/kg and 0.4 µg/kg of the short peptide P10581, respectively. 30 min later, the groups A-F were further injected with 5 mg/kg of the morphine, and 1 h later, the PWT of each group was recorded.

(2) Each group was injected with the drug in the afternoon on the $6^{th}$ day after modeling, and from the $7^{th}$ day to the $10^{th}$ day, the drug administration was performed at 9:00 a.m. and 5:30 p.m. (injected twice a day consecutively for 5 days), and the PWT of each group before and after the administration in the morning was measured every other day.

Figure 10A:
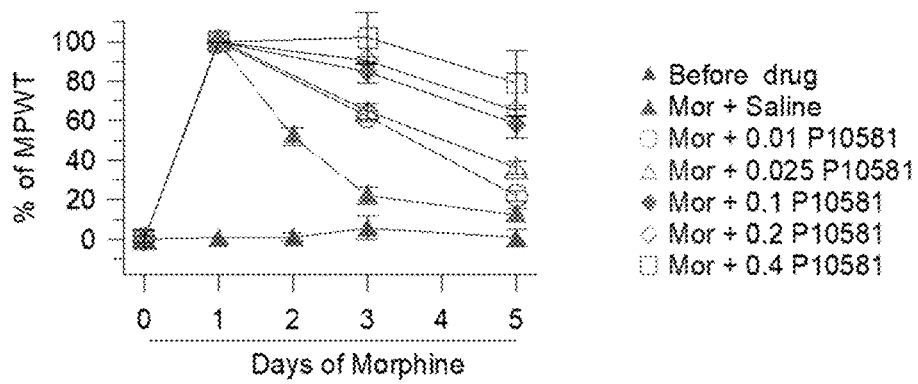
FIG. 10A illustrates normalized test results of an effect of the short peptide P10581 with different doses (0.01 µg/kg-0.40 µg/kg) on the morphine analgesic tolerance for neuropathic pain.
Figure 10B:
FIG. 10B illustrates the effect of different concentrations of the short peptide P10581 on the threshold of neuropathic pain after 3-day consecutive injection of morphine.

The effect of the short peptide P10581 with different doses (0.01 µg/kg-0.40 µg/kg) on the morphine analgesic tolerance for neuropathic pain after normalization was illustrated in FIG. 10A. FIG. 10B illustrated the effect of the short peptide P10581 with different doses on the morphine analgesic tolerance for neuropathic pain on the third day of consecutive injections.

In the FIG. 10B, ΔPWT (drug) and ΔPWT (Baseline) were calculated as follows:

ΔPWT(drug)=PWT(post-drug)−PWT(pre-drug); and

ΔPWT(Baseline)=PWT(before CCI)−PWT(after CCI).

The ΔPWT (drug) and ΔPWT (Baseline) involved in CCI-induced neuropathic pain model and BCP model can be calculated as above.

As shown in FIGS. 10A and 10B, the morphine analgesic tolerance for the neuropathic pain could be completely reversed in the presence of 0.4 µg/kg of the short peptide P10581.

Figure 11:
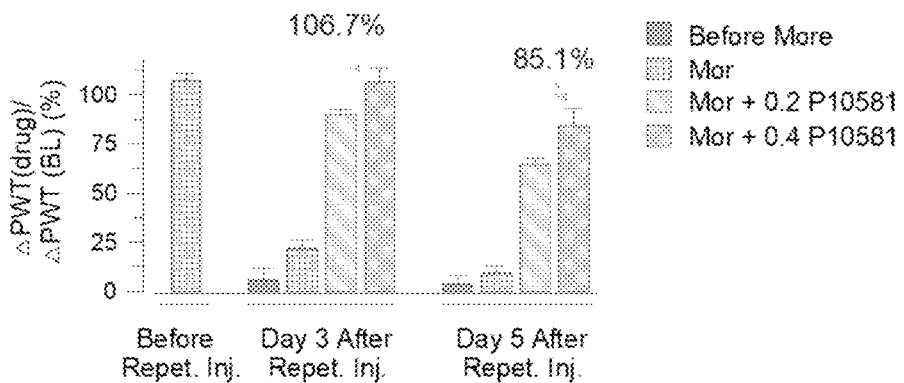
FIG. 11 illustrates a comparison of relieving effects of the short peptide in different doses (0.2 µg/kg and 0.4 µg/kg) on the morphine analgesic tolerance respectively after 3-day and 5-day consecutive injection of the morphine.

FIG. 11 illustrated a comparison of a relieving effect of the short peptide (0.2 µg/kg and 0.4 µg/kg) on the morphine analgesic tolerance after 3-day and 5-day consecutive injection of the morphine. The intensity of the relieving effect on the tolerance was represented by ΔPWT (drug)/ΔPWT (Baseline), where the ΔPWT (drug) indicated a difference between pain thresholds before and after Mor+P10581 injection in the morning. As shown in FIG. 11, different doses (0.01 µg/kg-0.40 µg/kg) of the short peptide P10581 generated different degrees of relieving effect on the morphine analgesic tolerance for neuropathic pain. Compared to the initial analgesic effect of the morphine (Before Rept. Inj. in FIG. 11), after the 3-day consecutive injection of morphine, 90.1% of the analgesic effect of the morphine could be restored by 0.2 µg/kg of the short peptide P10581, and 0.4 µg/kg of the short peptide P10581 could completely reverse the morphine analgesic tolerance. After 5-day continuous administration, the analgesic effect of the morphine almost completely disappeared, nevertheless, the analgesic effect could be restored to higher than 60% in the presence of 0.2 µg/kg of the short peptide P10581, and 0.4 µg/kg of the short peptide P10581 could restore the analgesic effect of the morphine by higher than 85%

Experimental Example 8 Analgesic Effect of Intrathecal Injection of Low-Dose Short Peptide P10581 on Mechanical Hyperalgesia in Neuropathic Pain Rat Model and its Effect on Morphine Analgesic Tolerance The analgesic effect of intrathecal injection of the low-dose short peptide P10581 (0.2 µg/kg) on mechanical hyperalgesia in a neuropathic pain rat model and its effect on the morphine analgesic tolerance were investigated herein.

This experiment was performed basically according to the steps of Experimental Example 4.

(1) 18 healthy adult SD rats, weighing 180-220 g, were selected to build a CCI-induced neuropathic pain model. On the $7^{th}$ day after modeling, those successfully-established models were randomly divided into 3 groups, where the group A was injected with normal saline; the group B was injected with morphine (15 µg, 10 µL); and the group C was injected with 0.2 µg/kg of the short peptide P10581, and then injected with morphine (15 µg, 10 µL) 30 min later. 1 h later, the PWT of each group was recorded.

(2) Each group was injected with the drug respectively at 9:00 a.m. and 5:30 p.m. from $7^{th}$ day to $11^{th}$ day after modeling, and the PWT of each group was measured before and after the administration in the morning every day.

Figure 12A:
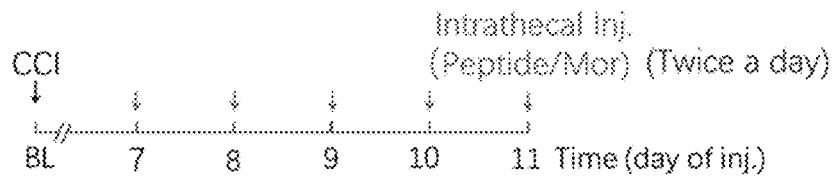
FIG. 12A schematically depicts intrathecal injection time points of the short peptide with a low dose (0.2 µg/kg) and the morphine (drug), where an arrow with CCI indicates a modeling time point; and other arrows indicate the intrathecal injection time point of the short peptide P10581 (Peptide) or the morphine.

FIG. 12A schematically depicted intrathecal injection time points of the low-dose short peptide with (0.2 µg/kg) and morphine (drug), where an arrow with CCI indicated a modeling time point; and other arrows indicated the intrathecal injection time point of the short peptide P10581 (Peptide) or morphine.

Figure 12B:
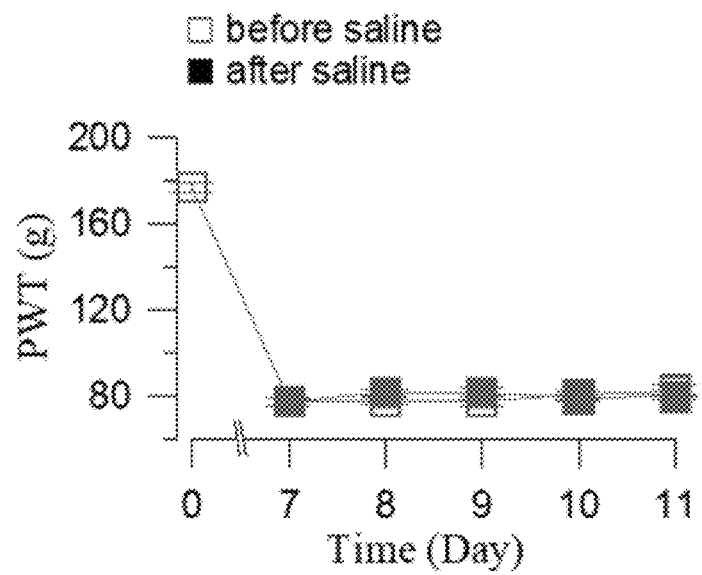
FIG. 12B illustrates an analgesic effect of the intrathecal injection of a normal saline (control group) on neuropathic pain.
Figure 12C:
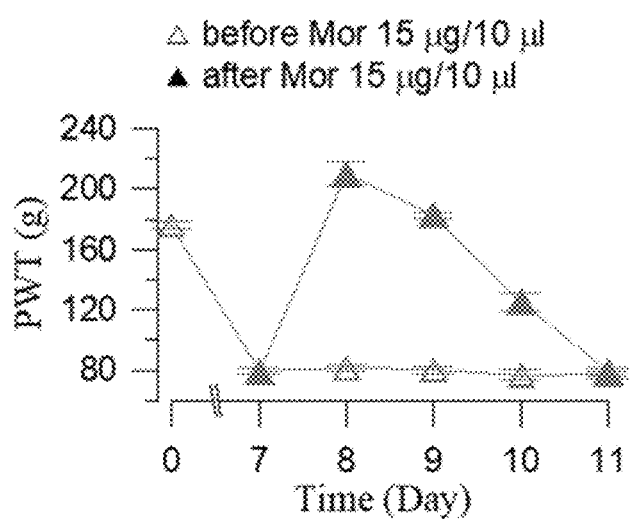
FIG. 12C illustrates an analgesic effect of the intrathecal injection of morphine on neuropathic pain.
Figure 12D:
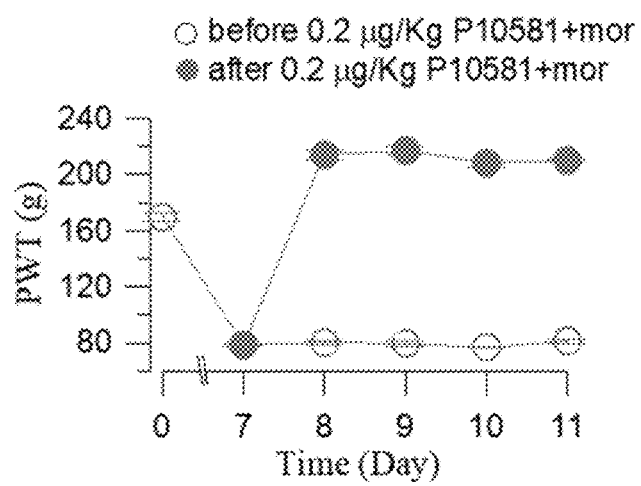
FIG. 12D illustrates an effect of the intrathecal injection of low-dose short peptide P10581 (0.2 µg/kg) on the morphine analgesic tolerance.

The analgesic effect of intrathecal injection of normal saline (control group) on neuropathic pain was illustrated in FIG. 12B. FIG. 12C illustrated an analgesic effect of intrathecal injection of morphine on neuropathic pain. FIG. 12D illustrated an effect of intrathecal injection of the low-dose short peptide P10581 (0.2 µg/kg) on the morphine analgesic tolerance for neuropathic pain. As shown in FIG. 12C, after 4-day consecutive intrathecal administration of the morphine (15 µg, 10 µL, twice a day), the analgesic effect of the morphine on neuropathic pain completely disappeared. As shown in FIG. 12D, the morphine analgesic tolerance for neuropathic pain could be completely eliminated by the intrathecal injection of low-dose short peptide P10581 (0.2 µg/kg).

The Experimental Examples 4-8 demonstrated that the morphine analgesic tolerance in animals can be effectively relieved through the administration of 0.01 µg/kg or more of the short peptide P10581. The 0.01-0.40 µg/kg of the short peptide P10581 had different degrees of relieving effect on the morphine analgesic tolerance, and when the dose reached 0.40 µg/kg, the morphine analgesic tolerance can be completely eliminated, and the analgesic effect of the morphine can be maintained. Interestingly, the single administration of 7.2-8.0 µg/kg of the short peptide P10581 also exhibited excellent analgesic effect on neuropathic pain in rats without generating the tolerance. The morphine analgesic tolerance for neuropathic pain can be effectively eliminated through intrathecal injection of 0.20 µg/kg of the short peptide P10581.

Therefore, the short peptide P10581 provided herein can completely eliminate the morphine analgesic tolerance for neuropathic pain even in a low dose (0.01-0.40 µg/kg) while maintaining the analgesic effect of the morphine. Under an administration dose of 7.2-8.0 µg/kg, the short peptide P10581 also exhibited an analgesic effect similar to that of the morphine without developing the analgesic tolerance after repeated administration.

Experimental Example 9 Analgesic Effect and Tolerance of Short Peptide P10581 and Morphine on Mechanical Hyperalgesia in BCP Rat Model The analgesic effect and tolerance of the short peptide P10581 and morphine on BCP in rats were explored herein.

(S1) Healthy adult SD rats, weighing 180-220 g, were selected, numbered on tails and transferred to the same cage (15 rats in total).

(S2) The rats were maintained in the measuring room for 2 h for adaptation. After the rats became quiet, the tapered tip of the 38500-PAM system was aimed at the plantar center of the left hind paw of the rats to measure PWT at a constant force rate (30 gf/s), with a maximum measurement time of 15 s (a measured value greater than 450 gf will cause damage to rats).

(S3) The PWT was recorded when a left hind paw of the rats showed withdrawal reflex, and if the rat did not generate the withdrawal response after 15 s, the measurement was stopped. The measurement was repeated 3-5 times for each rat with an interval of 5-10 min, and the results were averaged. The rats were allowed to rest for several hours to build a BCP model.

(S4) The PWT was measured from the $3^{rd}$ day after modeling, and the PWT decreased to the minimum on the $18^{th}$ day. Those unsuccessful models were removed, and on the $22^{nd}$ day after modeling, the successfully-established models were randomly divided into 3 groups, where the groups A-C were subcutaneously with normal saline, 14.4 μg/kg of the short peptide P10581 and 5 mg/kg of morphine, respectively. 1.5 h later, the PWT of the right hind paw of each group was measured. Each rat was measured 3-5 times with an interval of 5-10 min, and the PWTs were averaged as the practical PWT (unit: g). The drug administration was performed twice a day (at 9:30 a.m. and 4:30 p.m.) for consecutive 4 days, and the PWT of each group before and after administration was measured in the morning every day. The group C was subcutaneously injected with 14.4 μg/kg of the short peptide P10581 on the $26^{th}$ day, and 1.5 h later, the PWT of the right hind paw was recorded.

Figure 13:
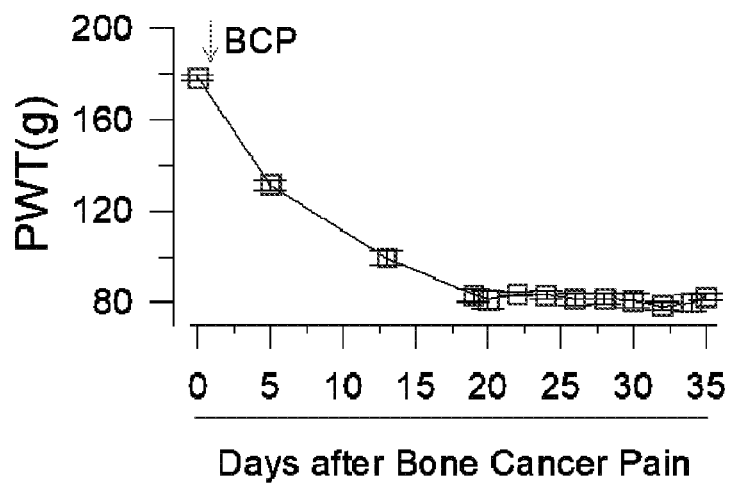
FIG. 13 illustrates test results of PWT after a BCP rat model is established.

The PWT of the BCP rat model was illustrated in FIG. 13, from which it can be seen that the PWT reached the minimum on the $18^{th}$ after the modeling.

Figure 14A:
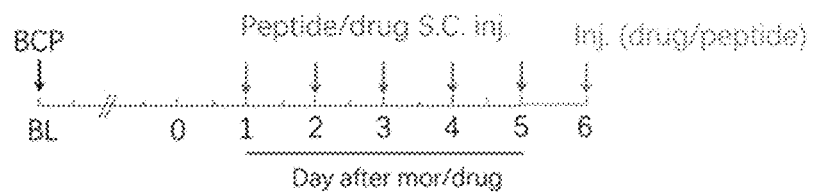
FIG. 14A schematically depicts the injection time points of the short peptide P10581 (Peptide) and morphine (drug), where an arrow with BCP indicates a modeling time point; and a solid arrow indicates the injection time point of the short peptide P10581 (Peptide) or the morphine (drug)
Figure 14B:
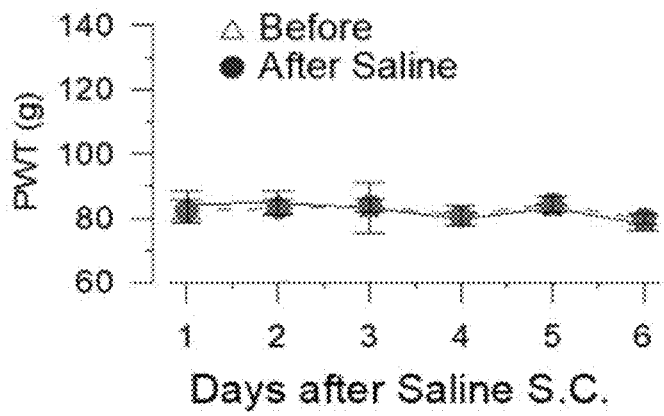
FIG. 14B illustrates an analgesic effect of the normal saline (control group) on BCP.
Figure 14C:
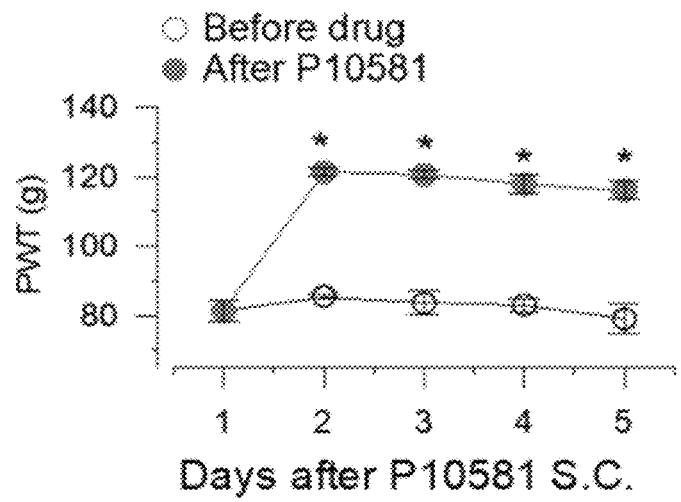
FIG. 14C illustrates an analgesic effect of the short peptide P10581 on BCP, where **, $P<0.001$; and *, $P<0.01$.
Figure 14D:
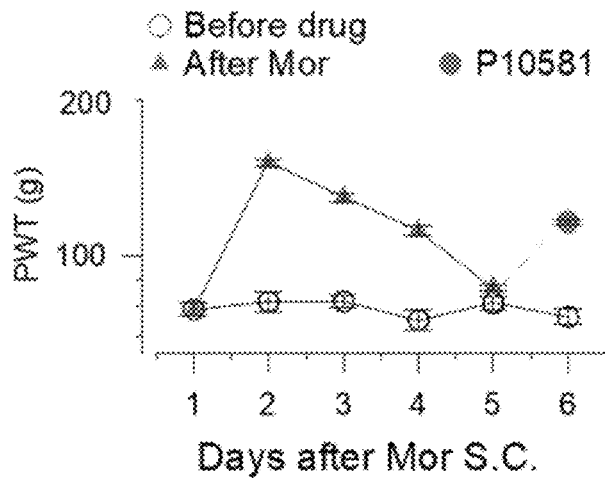
FIG. 14D illustrates an analgesic effect of repeated injection of the morphine followed by injection of the short peptide P10581 on BCP.

FIG. 14A schematically depicted the injection time points of the short peptide P10581 (Peptide) and morphine (drug), where an arrow with BCP indicated the modeling time point; a solid arrow indicated the injection time point of the short peptide P10581 (Peptide) or the morphine (drug). FIG. 14B illustrated an analgesic effect of the saline (control group) on BCP. FIG. 14C illustrated an analgesic effect of the short peptide P10581 on BCP, where **, P<0.001; and *, P<0.01. FIG. 14D illustrated an analgesic effect of repeated injection of the morphine followed by injection of the short peptide P10581 on BCP.

As shown in FIG. 14C, the repeated injection of the short peptide P10581 (i.d. 14.4 μg/kg, twice a day) can significantly alleviate the BCP of rats without developing the analgesic tolerance after consecutive 4-day administration. As shown in FIG. 14D, the analgesic effect of morphine on BCP decreased gradually after repeated injection (5 mg/kg, i.d.), and disappeared at day 4, confirming the occurrence of morphine analgesic tolerance for BCP in rats.

Experimental Example 10 Analgesic Effect of Low-Dose Short Peptide P10581 on Mechanical Hyperalgesia in BCP Rat Model and its Effect on Morphine Analgesic Tolerance The analgesic effect of the low-dose short peptide P10581 (0.20-0.40 μg/kg) on mechanical hyperalgesia in a BCP rat model and its effect on the morphine analgesic tolerance were investigated herein.

This experiment was performed basically according to the steps of Experimental Example 9.

The successfully-established BCP model rats were divided into 4 groups randomly on the $22^{nd}$ day after modeling, where the group A was injected with 0.2 μg/kg of the short peptide P10581; the group B was injected with 0.2 μg/kg of the short peptide P10581, and injected with 5 mg/kg of the morphine 30 min later; the group C was injected with 0.4 μg/kg of the short peptide P10581; and the group D was injected with 0.4 μg/kg of the short peptide P10581, and injected with 5 mg/kg of the morphine 30 min later. 1 h later, the PWT of the right hind paw of each group was recorded. Each of the rats was measured 3-5 times with an interval of 5-10 min, and the PWTs were averaged to taken as the practical PWT (unit: g). The drug administration was performed twice a day (at 9:30 a.m. and 4:30 p.m.) for consecutive 4 days, and the PWT of each group before and after the administration in the morning was measured. Test results were shown in FIGS. 15A-16D.

Figure 15A:
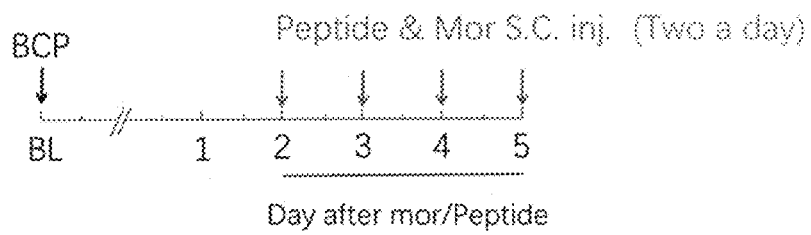
FIG. 15A schematically depicts subcutaneous (S.C.) injection time points of the low-dose short peptide P10581 (0.2 µg/kg) and the morphine, where an arrow with BCP indicates a modeling time point; and other arrows indicate the S.C. injection time point of the short peptide P10581 (Peptide) or the morphine (Mor)

FIG. 15A schematically depicted a subcutaneous (S.C.) injection time point of the low-dose short peptide P10581 (0.2 μg/kg) and morphine, where an arrow with BCP indicated a modeling time point; and other arrows indicated the S.C. injection time point of the short peptide P10581 (Peptide) or morphine (drug).

Figure 15B:
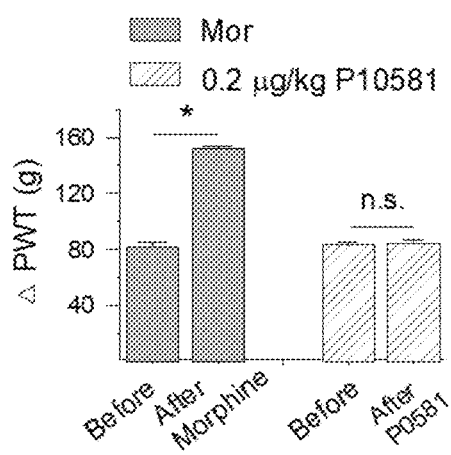
FIG. 15B illustrates a comparison of analgesic effects of repeated S.C. injection of morphine and the low-dose short peptide P10581 (0.2 μg/kg) on BCP.

FIG. 15B illustrates a comparison of analgesic effects of repeated S.C. injection of the morphine and the low-dose short peptide P10581 (0.2 μg/kg) on BCP in rats. As shown in FIG. 15B, no analgesic effect was observed on BCP through the subcutaneous injection of the low-dose short peptide P10581 (0.2 μg/kg), whereas the BCP in rats was significantly alleviated by the subcutaneous injection of morphine.

Figure 15C:
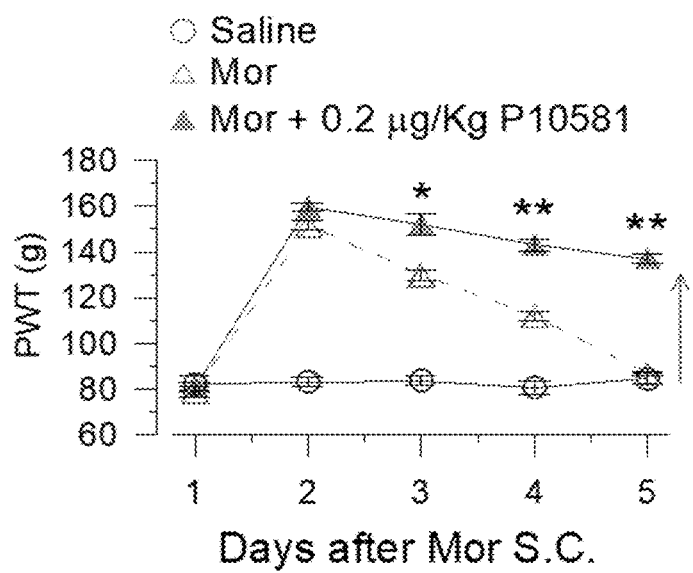
FIG. 15C schematically depicts an effect of the low-dose short peptide P10581 (0.2 μg/kg) on the morphine analgesic tolerance for BCP, where the morphine (Mor) group is a positive control group.
Figure 15D:
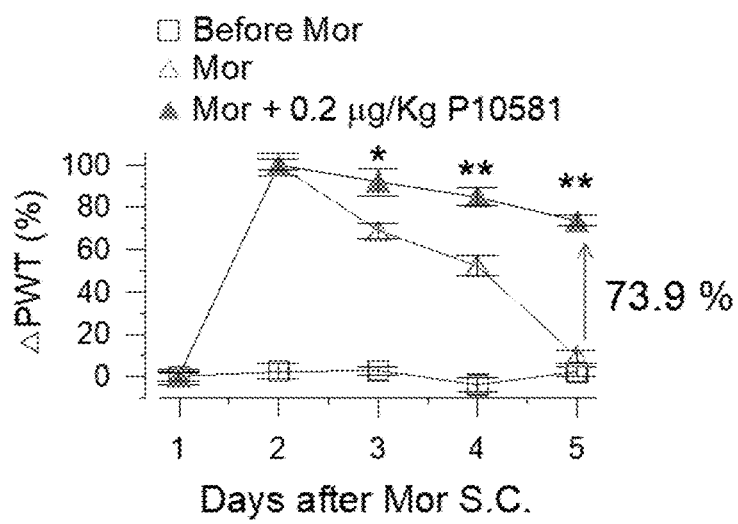
FIG. 15D schematically depicts an effect of the low-dose short peptide P10581 (0.2 μg/kg) on the morphine analgesic tolerance for BCP after normalization, where *, P<0.01; and **, P<0.001 vs. Mor.

The effect of the low-dose short peptide P10581 (0.2 μg/kg) on the morphine analgesic tolerance for BCP was depicted in FIG. 15C, where the group morphine (Mor) was a positive control group. FIG. 15D schematically depicted an effect of the low-dose short peptide P10581 (0.2 μg/kg) on the morphine analgesic tolerance for BCP after normalization, where *, P<0.01; and **, P<0.001 vs. Mor.

ΔPWT (%) in FIG. 15D was calculated as follows:

$$\Delta PWT(\%)=100*\{[PWT(post\text{-}drug)-PWT(pre\text{-}drug)]/\Delta PWT(Maxi)\}(\%):$$

As shown in FIGS. 15C and 15D, the analgesic effect of the morphine on BCP experienced a gradual decline after the repeated subcutaneous (5 mg/kg through S.C., twice a day), and after the consecutive 4-day administration, the morphine completely lost the analgesic effect on BCP. Nevertheless, the PWT was significantly increased when the low-dose short peptide P10581 (0.2 μg/kg) was injected before the administration of 5 mg/kg morphine, and the 0.2 μg/kg short peptide P10581 can reverse the morphine analgesic tolerance for BCP by 73.9%, demonstrating that the low-dose short peptide P10581 (0.2 µg/kg) can effectively relieve the tolerance to the morphine analgesic effect on BCP.

Figure 16A:
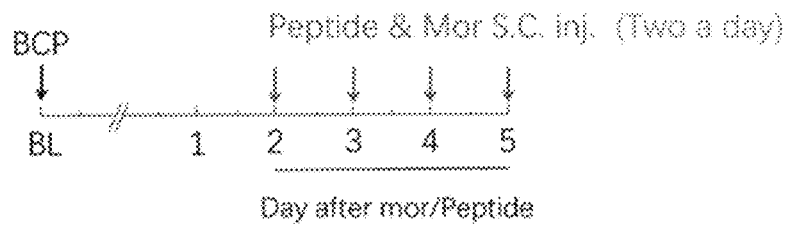
FIG. 16A schematically depicts S.C. injection time points of the low-dose short peptide P10581 (0.4 μg/kg) and morphine (Mor), where an arrow with BCP indicates a modeling time point; and other arrows indicate the S.C. injection time point of the short peptide P10581 (Peptide) or morphine (Mor)

FIG. 16A schematically depicted injection time points of the low-dose short peptide P10581 (0.4 µg/kg) and morphine (Mor), where an arrow with BCP indicated a modeling time point; and other arrows indicated the S.C. injection time point of the short peptide P10581 (Peptide) or the morphine (Mor).

Figure 16B:
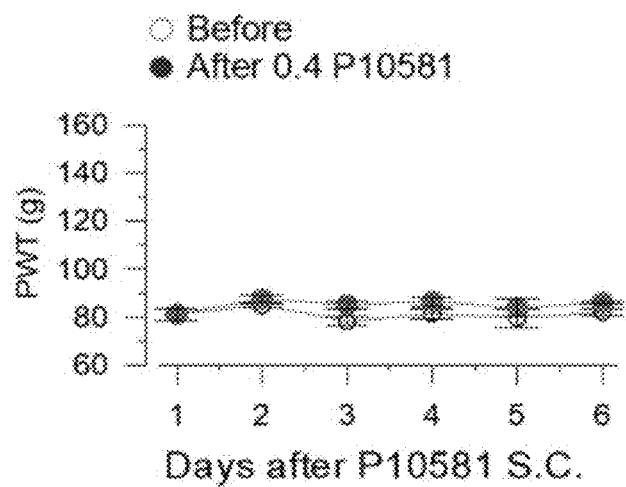
FIG. 16B illustrates a comparison of analgesic effects of repeated S.C. injection of the morphine and the low-dose short peptide P10581 (0.4 μg/kg) on BCP.

The analgesic effects of repeated S.C. injection of the morphine and the low-dose short peptide P10581 (0.4 µg/kg) on BCP were compared in FIG. 16B, from which it can be observed that the short peptide P10581 had no analgesic effect on BCP in a S.C. administration dose of 0.4 µg/kg.

Figure 16C:
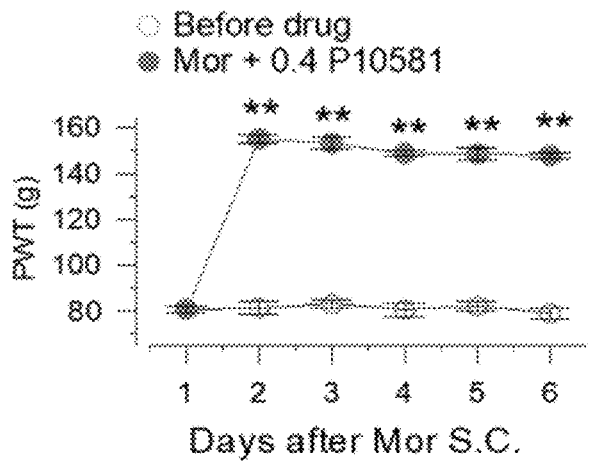
FIG. 16C schematically depicts an effect of the low-dose short peptide P10581 (0.4 μg/kg) on the morphine analgesic tolerance for BCP, where **: P<0.001 vs. Before drug.
Figure 16D:
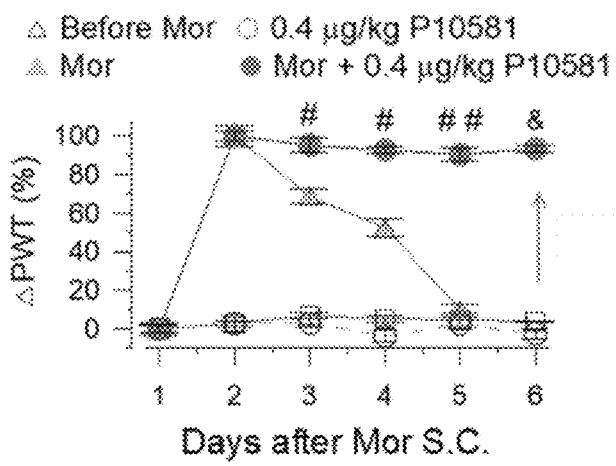
FIG. 16D schematically depicts an effect of the low-dose short peptide P10581 (0.2 μg/kg) on the morphine analgesic tolerance for BCP after normalization, where #: P<0.01 vs. Mor, ##: P<0.001 vs. Mor, and &: P<0.001 vs. before Mor.

FIG. 16C schematically depicted an effect of the low-dose short peptide P10581 (0.4 µg/kg) on the morphine analgesic tolerance for BCP, where **: P<0.001 vs. Before drug. FIG. 16D schematically depicted an effect of the low-dose short peptide P10581 (0.4 µg/kg) on the morphine analgesic tolerance for BCP after normalization, where #: P<0.01 vs. Mor; ##: P<0.001 vs. Mor; and &: P<0.001 vs. before Mor. As shown in FIGS. 16C and 16D, the analgesic effect of the morphine on BCP can be completely restored through the repeated S.C. injection of 0.4 µg/kg of the short peptide P10581.

The results of Experimental Examples 9 and 10 confirmed that the morphine analgesic tolerance for BCP in animals can be effectively eliminated through the administration of 0.20 µg/kg or more of the short peptide P10581. The 0.20-0.40 µg/kg of the short peptide P10581 had different degrees of relieving effect on the morphine analgesic tolerance. Under an administration dose of 0.40 µg/kg, the short peptide P10581 can completely eliminate the morphine analgesic tolerance and maintain the analgesic effect of the morphine. The single administration of 14.4 µg/kg of the short peptide P10581 had an excellent analgesic effect on BCP in rat without generating the tolerance.

Therefore, the low-dose administration (0.20-0.40 µg/kg) of the short peptide P10581 provided herein could completely eliminate the morphine analgesic tolerance for BCP and maintain the analgesic effect of the morphine. Moreover, the administration of 14.4 µg/kg of the short peptide P10581 can reach an analgesic effect similar to that of the morphine without developing the tolerance after repeated administration.

Comparative Example 1 Analgesic Effect and Tolerance of Short Peptide P10583 and Morphine on Mechanical Hyperalgesia in Inflammatory Pain Rat Model The analgesic effect and tolerance of the short peptide P10583 and morphine on mechanical hyperalgesia in an inflammatory pain rat model were investigated herein.

(S1) A total of 20 healthy adult SD rats (half male and half female), weighing 180-220 g, were selected, numbered on tails and transferred to the same cage.

(S2) The rats were maintained in a measuring room for 2 h for adaptation. After the rats became quiet, the tapered tip of the 38500-PAM system was aimed at a plantar center of the left hind paw of the rats to measure PWT at a constant force rate (30 gf/s), with a maximum measurement time of 15 s (a measured value greater than 450 gf will cause damage to rats).

(S3) The PWT was recorded when a left hind paw of the rats showed withdrawal reflex, and if the rat did not generate the withdrawal response after 15 s, the measurement was stopped. The measurement was repeated 3-5 times for each rat with an interval of 5-10 min. The results of multiple PWT measurements were averaged as the Baseline (BL) (unit: g). After that, 6 µL of 1 wt % Carr was intradermally injected into the plantar surface of the hind paw to build an inflammatory pain rat model.

(S4) The PWT of the left hind paw of each rat was measured 1 h after the Carr injection. Rats with a higher inflammatory threshold and rats with a lower inflammatory threshold were mixed and equally divided into four groups (group A, group B, group C and group D), each for five rats, such that any two groups of rats had similar distribution of inflammatory threshold. The groups A, B, C and D were intradermally injected with normal saline (as a control group), 5 mg/kg of morphine, 2 µg/kg of the short peptide P10583 and 2 µg/kg of the short peptide P10581, respectively, at the plantar surface of the left hind paw. 1 h later, the PWT of the left hind paw of the rats in each group was measured 3-5 times at an interval of 5-10 min. The multiple PWT measurement results were averaged to be considered as the practical PWT (with a unit of g). Then the drug was injected every 2 h according to the above-mentioned administration dose and time, and the corresponding PWT was recorded (six times in total).

P10581: WKCNPNDDKCCRPKLKC (shown as SEQ ID NO: 1)

P10583: WKCNPNDDKCR (shown as SEQ ID NO: 4).

Figure 17A:
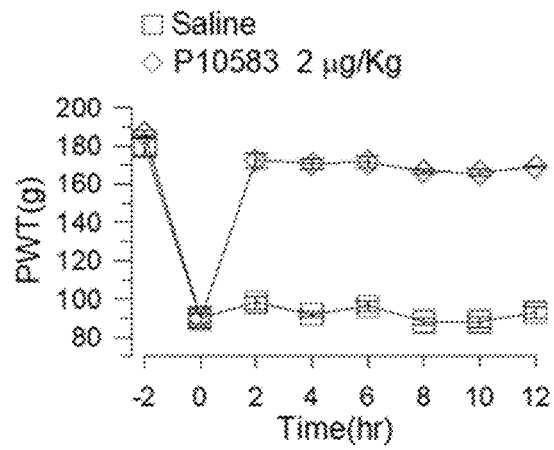
FIG. 17A illustrates test results of an inhibitory effect of a short peptide P10583 on mechanical hyperalgesia in rats and its analgesic tolerance.

The test results of an inhibitory effect of a short peptide P10583 on mechanical hyperalgesia in rats and its analgesic tolerance were shown in FIG. 17A. The test results of an inhibitory effect of the morphine on mechanical hyperalgesia in rats and its analgesic tolerance were shown in FIG. 17B. FIG. 17C illustrated a comparison of the analgesic tolerance of the short peptide P10583 and morphine for mechanical hyperalgesia in rats after normalization.

Figure 17B:
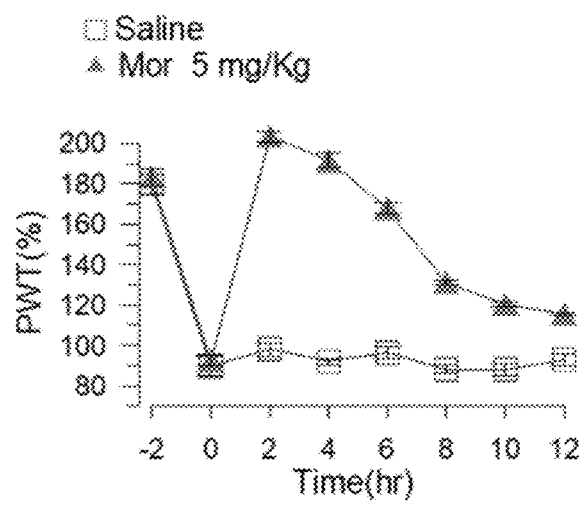
FIG. 17B illustrates test results of an inhibitory effect of the morphine on mechanical hyperalgesia in rats and its analgesic tolerance.
Figure 17C:
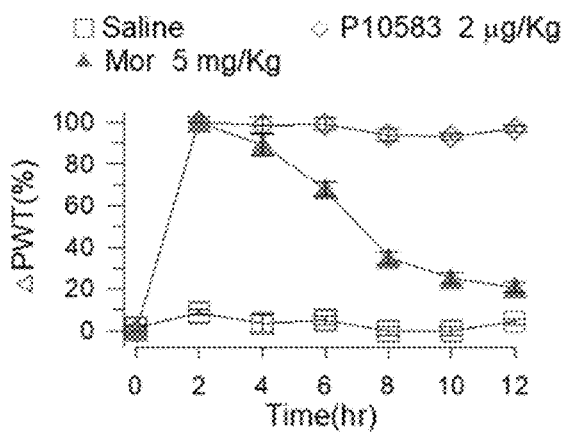
FIG. 17C illustrates a comparison of the analgesic tolerance of the short peptide P10583 and morphine for mechanical hyperalgesia in rats after normalization.

As shown in FIGS. 17A-17C, the analgesic effect of the short peptide P10583 (2 µg/kg) of the disclosure was similar to the short peptide P10581 herein, both of which can completely reverse the Carr-induced inflammatory pain threshold and the analgesic effect can last for more than 12 h, which indicated that the short peptide P10583 and the short peptide P10581 exhibited an excellent analgesic effect on the mechanical pain in rats without developing the analgesic tolerance. As a positive control group, the morphine (5 mg/kg) showed a gradually declined analgesic effect with the increase in the number of injections, which demonstrated the occurrence of the morphine-induced analgesic tolerance.

Comparative Example 2 Analgesic Effect of Low-Dose Short Peptide P10583 on Mechanical Hyperalgesia in Inflammatory Pain Rat Model and Effect of Low-Dose Short Peptide P10583 on Morphine Analgesic Tolerance The analgesic effect of a short peptide P10583 in a dose of 0.10 µg/kg on mechanical hyperalgesia in the inflammatory pain rat model and an effect of the short peptide P10583 on the morphine analgesic tolerance were investigated herein.

This experiment was performed basically according to the steps of Control Experiment 1.

(1) 20 healthy adult SD rats, weighing 180-220 g, were selected, injected with 1 wt % Carr solution and divided into 4 groups randomly and averagely (i.e., groups A-D). The group A was injected with normal saline; the group B was intradermally injected with 0.1 µg/kg of the short peptide P10583; the group C was injected with morphine; and the group D was a group of P10583+morphine (Mor) which was intradermally injected with 0.1 μg/kg of the short peptide P10583 and then with 5 mg/kg of morphine 30 min later through the plantar surface of the left hind paw. 1 h later, the PWT of each group was recorded when the mechanical withdrawal of the left hind paw occurred, and each rat was measured 3-5 times at an interval of 5-10 min.

(2) The drug was injected every 2 h according to the dose and time adopted in the first administration (seven injections in total), and the PWT was recorded.

Figure 18A:
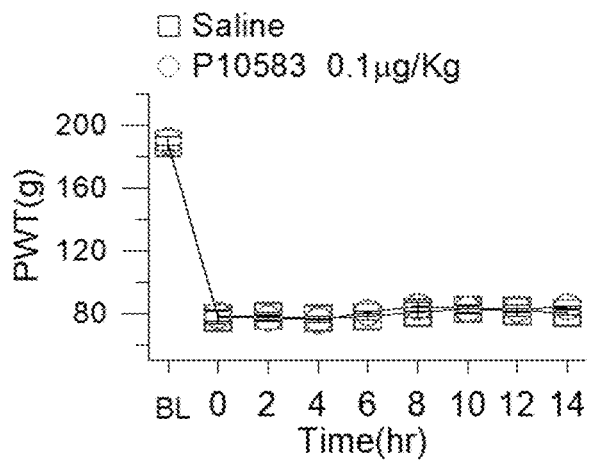
FIG. 18A illustrates test results of an inhibitory effect of the low-dose short peptide P10583 (0.10 μg/kg) on mechanical hyperalgesia in rats and its analgesic tolerance.

The test results of an inhibitory effect of the low-dose short peptide P10583 (0.10 μg/kg) on mechanical hyperalgesia in rats and its analgesic tolerance were shown in FIG. 18A. The relieving effect of the low-dose short peptide P10583 (0.10 μg/kg) on the morphine analgesic tolerance was shown in FIG. 18B, where the morphine group was a control group. FIG. 18C illustrated a comparison of relieving effects of the low-dose short peptide P10583 (0.10 μg/kg) and the low-dose short peptide P10581 (0.05 μg/kg and 0.10 μg/kg) on the morphine analgesic tolerance.

Figure 18B:
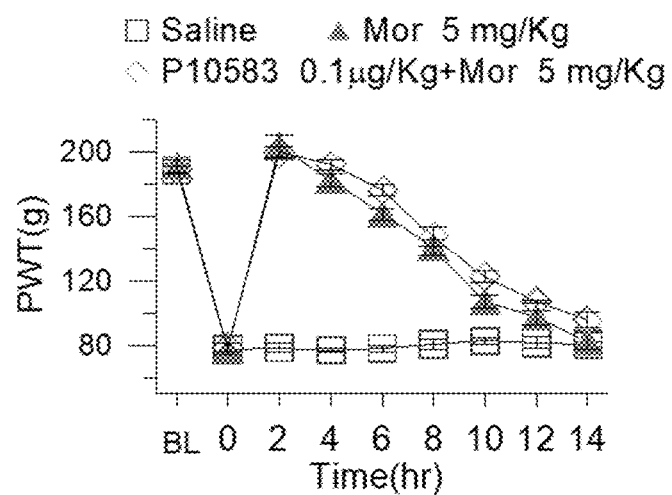
FIG. 18B illustrates test results of a relieving effect of the low-dose short peptide P10583 (0.10 μg/kg) on the morphine analgesic tolerance.
Figure 18C:
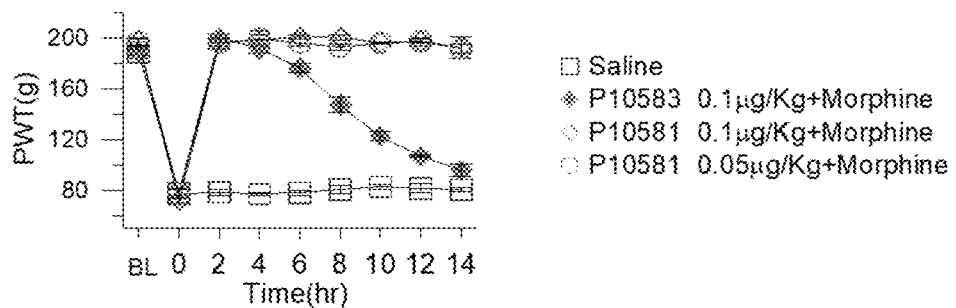
FIG. 18C illustrates a comparison of relieving effects of the low-dose short peptide P10583 (0.10 μg/kg) and the low-dose short peptide P10581 (0.05 μg/kg and 0.10 μg/kg) on the morphine analgesic tolerance.

As shown in FIGS. 18A-18C, no relieving effect of the low-dose short peptide P10583 (0.10 μg/kg) on the morphine analgesic tolerance was observed, whereas the same-dose short peptide P10581 (0.10 μg/kg) completely eliminated the tolerance to morphine the analgesic effect. Moreover, even a lower-dose short peptide P10581 (0.05 μg/kg) can completely eliminate the morphine analgesic tolerance for mechanical hyperalgesia in rats.

It should be noted that as verified by clinical tests, an administration dose of the short peptide P10581 for human is 1/6.3-1/10 times an administration dose of the short peptide for animal when the short peptide P10581 is utilized to inhibit the development of morphine tolerance. For example, for the treatment of inflammatory pain, the administration dose of the short peptide P10581 for animal is 0.05-0.10 μg/kg, while the administration dose of the short peptide P10581 for human is 0.005-0.0159 μg/kg. In a treatment of neuropathic pain, the administration dose of the short peptide P10581 for animal is 0.01-0.40 μg/kg, while the administration dose of the short peptide P10581 for human is 0.001-0.0635 μg/kg. In the treatment of BCP, the administration dose of the short peptide P10581 for animal is 0.20-0.40 μg/kg, while for human is 0.02-0.0635 μg/kg.

It has still been less reported about the mechanism and clinical trial of morphine tolerance, there is still a lack of effective clinical measures to inhibit the morphine tolerance. Surprisingly, the short peptide P10581 provided herein has an excellent analgesic effect when administered alone without generating tolerance after repeated administration. More importantly, the short peptide P10581 has also been demonstrated to be capable of relieving or even eliminating the morphine analgesic tolerance in a low dose. In the method provided herein, the short peptide and the morphine are administered together to a subject in need; or the short peptide is injected to the subject and then morphine is injected; or a pharmaceutical composition including the short peptide and morphine is administered to the subject. The short peptide is a peptide consisting of an amino acid sequence shown in SEQ ID NO: 1 or a pharmaceutically-acceptable salt thereof. The pharmaceutical composition and method provided herein can effectively and stably relieve and eliminate the morphine tolerance while maintaining the analgesic effect of morphine, and provide a reference for the clinical treatment of morphine tolerance and development of related drugs.

Described above are merely some embodiments of the disclosure, which are not intended to limit the disclosure. Technical parameters not described in detail can vary in the range listed herein to obtain the same or similar technical effects. It should be understood that modifications, changes and replacements made by those skilled in the art without departing from the spirit of the disclosure shall fall within the scope of the disclosure defined by the appended claims.

What is claimed is:

1. A method for relieving or eliminating morphine-induced analgesic tolerance in a subject in need thereof, comprising:
   simultaneously administering a short peptide and morphine to the subject; or
   administering the short peptide to the subject followed by administration of morphine; or
   administering a pharmaceutical composition to the subject;
   wherein the pharmaceutical composition comprises:
   a therapeutically effective amount of the short peptide and morphine as active ingredients; and
   a pharmaceutically-acceptable salt or carrier; and
   the short peptide is a peptide consisting of the amino acid sequence of SEQ ID NO: 1 or a pharmaceutically-acceptable salt thereof.

2. The method of claim 1, wherein the subject is human or animal.

3. The method of claim 1, wherein a type of pain for the morphine to relieve is inflammatory pain; and an administration dose of the short peptide for an animal is not less than 0.05 µg/kg.

4. The method of claim 3, wherein the administration dose of the short peptide for the animal is 0.05-0.10 µg/kg.

5. The method of claim 3, wherein an administration dose of the short peptide for a human is 1/6.3-1/10 times the administration dose of the short peptide for the animal.

6. The method of claim 1, wherein a type of pain for the morphine to relieve is neuropathic pain; and an administration dose of the short peptide is not less than 0.01 µg/kg.

7. The method of claim 6, wherein the administration dose of the short peptide is 0.01-0.40 µg/kg.

8. The method of claim 6, wherein an administration dose of the short peptide for a human is 1/6.3-1/10 times an administration dose of the short peptide for an animal.

9. The method of claim 1, wherein a type of pain for the morphine to relieve is bone cancer pain (BCP); and an administration dose of the short peptide is not less than 0.20 µg/kg.

10. The method of claim 9, wherein the administration dose of the short peptide is 0.20-0.40 µg/kg.

11. The method of claim 9, wherein an administration dose of the short peptide for a human is 1/6.3-1/10 times an administration dose of the short peptide for an animal.

* * * * *